(12) United States Patent
Loccufier et al.

(10) Patent No.: US 8,530,510 B2
(45) Date of Patent: Sep. 10, 2013

(54) POLYMERIZABLE PHOTOINITIATORS AND RADIATION CURABLE COMPOSITIONS

(75) Inventors: Johan Loccufier, Zwijnaarde (BE); Roland Claes, Dendermonde (BE); Jaymes Van Luppen, Wilrijk (BE)

(73) Assignee: Agfa Graphics NV, Mortsel (BE)

( * ) Notice: Subject to any disclaimer, the term of this patent is extended or adjusted under 35 U.S.C. 154(b) by 240 days.

(21) Appl. No.: 13/060,278

(22) PCT Filed: Sep. 4, 2009

(86) PCT No.: PCT/EP2009/061444
§ 371 (c)(1),
(2), (4) Date: Feb. 23, 2011

(87) PCT Pub. No.: WO2010/029017
PCT Pub. Date: Mar. 18, 2010

(65) Prior Publication Data
US 2011/0195198 A1 Aug. 11, 2011

Related U.S. Application Data

(60) Provisional application No. 61/095,321, filed on Sep. 9, 2008.

(30) Foreign Application Priority Data

Sep. 9, 2008 (EP) .................... 08105272

(51) Int. Cl.
*A61K 31/381* (2006.01)
*C07D 335/16* (2006.01)

(52) U.S. Cl.
USPC ........................................... 514/434; 549/27

(58) Field of Classification Search
USPC ........................................... 514/434; 549/27
See application file for complete search history.

(56) References Cited

U.S. PATENT DOCUMENTS 4,390,676 A 6/1983 Loshaek

FOREIGN PATENT DOCUMENTS

| CN | 1727320 A | 2/2006 |
|---|---|---|
| EP | 0 377 191 A2 | 7/1990 |
| EP | 1 674 499 A1 | 6/2006 |
| JP | 2003-268048 A | 9/2003 |
| JP | 2004-224993 A | 8/2004 |
| JP | 2008-133486 A | 6/2008 |
| NL | 6409466 A | 2/1966 |
| WO | 03/033492 A1 | 4/2003 |

OTHER PUBLICATIONS

Official Communication issued in International Patent Application No. PCT/EP2009/061444, mailed on Nov. 3, 2009.
Compound w/ CAS Registry No. 601483-17-4, Database Registry Chemical Abstracts Service, Columbus, OH, Oct. 9, 2003. pp. 1-2.
Chiang et al., "Synthesis and Properties of Ultraviolet-Curable Resins Via a Thio-Ene (Thiol and Allyl) Addition Reaction," Journal of Applied Polymer Science, vol. 86, 2002, pp. 1878-1885.
Podkoscielna et al., "Use of a New Methacrylic Monomer, 4,4'-DI(2-Hydroxy-3-Methacryloyloxypropoxy) Benzophenone, In the Synthesis of Porous Microspheres," Journal of Polymer Science: Part A. Polymer Chemistry, vol. 44, 2006, pp. 7014-7026.
Loccufier et al., "Multifunctional Type II Photoinitiators and Curable Compositions", U.S. Appl. No. 12/992,610, filed Nov. 15, 2010.
Loccufier et al., "Polymerizable Type II Photoinitiators and Curable Compositions," U.S. Appl. No. 12/992,611, filed Nov. 15, 2010.
Loccufier et al., "Radiation Curable Compositions," U.S. Appl. No. 13/060,279, filed Feb. 23, 2011.

*Primary Examiner* — Taofiq A Solola
(74) *Attorney, Agent, or Firm* — Keating & Bennett, LLP

(57) ABSTRACT

A polymerizable Norrish Type II photoinitiators includes an optionally substituted benzophenone group or an optionally substituted thioxanthone group exhibiting improved compatibility with and solubility in radiation curable compositions. Radiation curable compositions and inkjet inks can contain these polymerizable Norrish Type II photoinitiators, exhibiting low extractable amounts of the photoinitiators and their residues after curing.

15 Claims, No Drawings

POLYMERIZABLE PHOTOINITIATORS AND RADIATION CURABLE COMPOSITIONS

BACKGROUND OF THE INVENTION

1. Field of the Invention

The present invention relates to a new type of photoinitiators and radiation curable compositions containing such photoinitiators, especially food compliant radiation curable compositions, and more specifically radiation curable inks and inkjet inks.

2. Description of the Related Art

A free radical photoinitiator initiates the polymerization of monomers when exposed to actinic radiation by the formation of a free radical. Photoinitiators are frequently used in UV-curable compositions, such as UV-curable inkjet inks.

Two types of free radical photoinitiators can be distinguished. A Norrish Type I initiator is an initiator which cleaves after excitation, yielding the initiating radical immediately. A Norrish Type II-initiator is a photoinitiator which is activated by actinic radiation and forms free radicals by hydrogen abstraction from a second compound that becomes the actual initiating free radical. This second compound is called a co-initiator or polymerization synergist.

A photoinitiator can be a monofunctional compound, but can also be a multifunctional compound, i.e. having more than one photoinitiating group. WO 03/033492 (COATES BROTHERS) discloses multifunctional thioxanthone photoinitiators.

When radiation curable compositions are used for food packaging, toys and dental applications, the amount of extractable residues is a critical issue and needs to be minimized. Low molecular weight products are usually not completely built into the polymer network and are prone to be readily extracted or to diffuse out of the cured composition.

Especially Norrish Type II initiators are a point of concern regarding extractable residues. Norrish Type II photo-initiators, such as benzophenone and thioxanthone, always require a co-initiator. Aliphatic tertiary amines, aromatic amines and thiols are preferred examples of co-initiators. After transfer of a hydrogen atom to the Norrish Type II initiator, the radical generated on the co-initiator initiates the polymerization. Theoretically the co-initiator is built into the polymer network. However, it is highly unlikely that both the hydrogen transfer and the initiation reaction yields are a hundred percent. Side reactions are likely to occur, resulting in unreacted co-initiator and side products being present in the cured composition. In food packaging printed upon with such a radiation curable composition, these low molecular weight residues remain mobile and if toxic will cause health risks upon being extracted into the food.

One approach to minimize extraction of the photoinitiator is to use Norrish Type II initiators with a higher molecular weight. However, polymeric initiators have a certain tendency to lose reactivity. Hence, often considerable amounts of polymeric initiators are required in order to reach the desired curing speed, thereby also increasing the viscosity to an undesirable level for a great number of applications using radiation curable compositions, such as e.g. inkjet printing.

EP 1674499 A (AGFA GRAPHICS) discloses radiation curable compositions and photoreactive polymers comprising a dendritic polymer core with at least one initiating functional group and at least one co-initiating functional group. While the use of a dendritic polymer core is advantageous for maintaining a low viscosity of the radiation curable composition, an improvement in curing speed is still desirable, especially in the absence of nitrogen inertisation.

Another approach in solving the extraction problem is to design a photoinitiator having one or more ethylenically unsaturated polymerizable groups so that it can be copolymerized with the other monomers of the radiation curable composition. However the copolymerization leads to a reduced mobility of the photoinitiator and hence a reduction in curing speed can be observed.

JP 2004-224993 (NIPPON KAYAKU) discloses self-photopolymerization type photopolymerization initiators for reducing its evaporation or sublimation from cured films of radiation curable compositions.

Another problem is that polymerizable Type II-initiators known in the prior art are only soluble to a limited extent in radiation curable formulations, resulting in a lower curing speed. In order to achieve sufficient curing speed, a mixture of polymerizable and non-polymerizable Type II-initiators initiators is used. For example, EBECRYL™ P36 from Cytec Surface Specialties is a polymerizable acrylated benzophenone further containing non-polymerizable benzophenone and hence considerable amounts of extractable photoinitiator and residues from cured compositions is observed.

JP 2003-268048 (NIPPON CATALYTIC CHEM) and JP 2008-133486 (NIPPON CATALYTIC CHEM) disclose resin compositions forming a layer having excellent properties as an ultraviolet shielding layer. The resin composition contains a polymer maintaining ultraviolet shielding ability for a long time which is made using a monomer having a benzotriazole ring or a benzophenone skeleton. Due to the hydroxy substitution in ortho position, the benzophenone compounds are UV-absorbers and do not function as photo-initiator. An example of such an UV-absorber can also be found in the Chemical Abstracts Database having CASRN 601483-16-3 as a reference.

Thus there still remains a need for Norrish Type II photoinitiators exhibiting good solubility in a broad range of radiation curable compositions, high reactivity with a low impact on the viscosity of the radiation curable composition and while still maintaining a low amount of extractable residues.

SUMMARY OF THE INVENTION

In order to overcome the problems described above, preferred embodiments of the present invention provide a polymerizable Norrish Type II photoinitiator as defined below.

Further preferred embodiments of the present invention provide radiation curable compositions including a co-initiator and the polymerizable Norrish Type II photoinitiator exhibiting good curing speed and low viscosity while maintaining low levels of extractable residues from a cured layer thereof.

Further advantages and embodiments of the present invention will become apparent from the following description.

DETAILED DESCRIPTION OF THE PREFERRED EMBODIMENTS

Definitions

The term "colorant", as used in the preferred embodiments of the present invention, means dyes and pigments.

The term "dye", as used in the preferred embodiments of the present invention, means a colorant having a solubility of 10 mg/L or more in the medium in which it is applied and under the ambient conditions pertaining.

The term "pigment" is defined in DIN 55943, herein incorporated by reference, as a colouring agent that is practically insoluble in the application medium under the pertaining ambient conditions, hence having a solubility of less than 10 mg/L therein.

The term "C.I." is used in the preferred embodiments of the present application as an abbreviation for Colour Index.

The term "alkyl" means all variants possible for each number of carbon atoms in the alkyl group i.e., for three carbon atoms: n-propyl and isopropyl; for four carbon atoms: n-butyl, isobutyl and tertiary-butyl; for five carbon atoms: n-pentyl, 1,1-dimethyl-propyl, 2,2-dimethylpropyl and 2-methylbutyl etc.

Polymerizable Norrish Type II Photoinitiators

A polymerizable Norrish Type II photoinitiator according to Formula (I):

Formula (I)

$$A\left(L_1\right)_n\left(\underset{\|}{C}\right)_m O-CH_2-CH(OR_1)-CH_2-O-L_2-O-\underset{\|}{C}-C(R_2)=CH_2$$

wherein
A represents a Norrish type II initiator selected from the group consisting of an optionally substituted benzophenone and an optionally substituted thioxanthone;
$L_1$ represents a divalent linking group, positioning the Norrish type II initiator moiety A and the C=O-group in a 1 to X position, where position 1 is defined as the atom in the aromatic ring of A to which $L_1$ is covalently bonded and position X is defined as the carbon atom of the C=O-group;
n represents 0 or 1;
m represents 0 or 1, with the proviso that n is equal to 0, when m is equal to 0;
X represents an integer selected from 3 to 7;
R1 is selected from the group consisting of a hydrogen, an optionally substituted alkyl group, an optionally substituted alkenyl group, an optionally substituted alkynyl group, an optionally substituted alkaryl group, an optionally substituted aralkyl group, an optionally substituted aryl group, an optionally substituted heteroaryl group and an acyl group;
R2 represents hydrogen or a methyl group;
$L_2$ represents a divalent linking group, selected from the group consisting of an optionally substituted saturated alkylene group, an optionally substituted unsaturated alkylene group, an optionally substituted arylene group and a group represented by Formula (II):

Formula (II)

$$\cdots\overset{R3}{\underset{R4}{C}}\left(O\overset{R6}{\underset{R5}{C}}\right)_p\cdots,$$

wherein
R3 to R6 independently represent hydrogen or a methyl group; and p represents an integer from 1 to 10.

In a preferred embodiment of the polymerizable Norrish Type II photoinitiator according to Formula (I), the integer n is 0.

In a preferred embodiment of the polymerizable Norrish Type II photoinitiator according to Formula (I), the divalent linking group $L_2$ represents an optionally substituted saturated alkylene group.

In a preferred embodiment of the polymerizable Norrish Type II photoinitiator according to Formula (I), the group R2 represents hydrogen.

In a more preferred embodiment of the polymerizable Norrish Type II photoinitiator according to Formula (I), the integer n is 0 and the divalent linking group $L_2$ represents an optionally substituted saturated alkylene group.

In a more preferred embodiment of the polymerizable Norrish Type II photoinitiator according to Formula (I), the integer n is 0 and the group R2 represents hydrogen.

In a more preferred embodiment of the polymerizable Norrish Type II photoinitiator according to Formula (I), the divalent linking group $L_2$ represents an optionally substituted saturated alkylene group and the group R2 represents hydrogen.

In the most preferred embodiment of the polymerizable Norrish Type II photoinitiator according to Formula (I), the integer n is 0, the group R2 represents hydrogen and the divalent linking group $L_2$ represents an optionally substituted saturated alkylene group.

In one embodiment, the polymerizable Norrish Type II photoinitiator may contain 2, 3 or more ethylenically unsaturated polymerizable groups.

In a preferred embodiment, the polymerizable Norrish Type II photoinitiator contains only one acrylate group, since multiple acrylate groups reduce the flexibility of a cured layer.

Preferred polymerizable Norrish Type II initiators containing a thioxanthone group are given below in Table 1, without being limited thereto.

TABLE 1

| TX-1 |
|---|
| (structure: thioxanthone with 1-carboxylate linked to –O–CH₂–CH(OH)–CH₂–O–(CH₂)₄–O–C(=O)–CH=CH₂) |

TABLE 1-continued
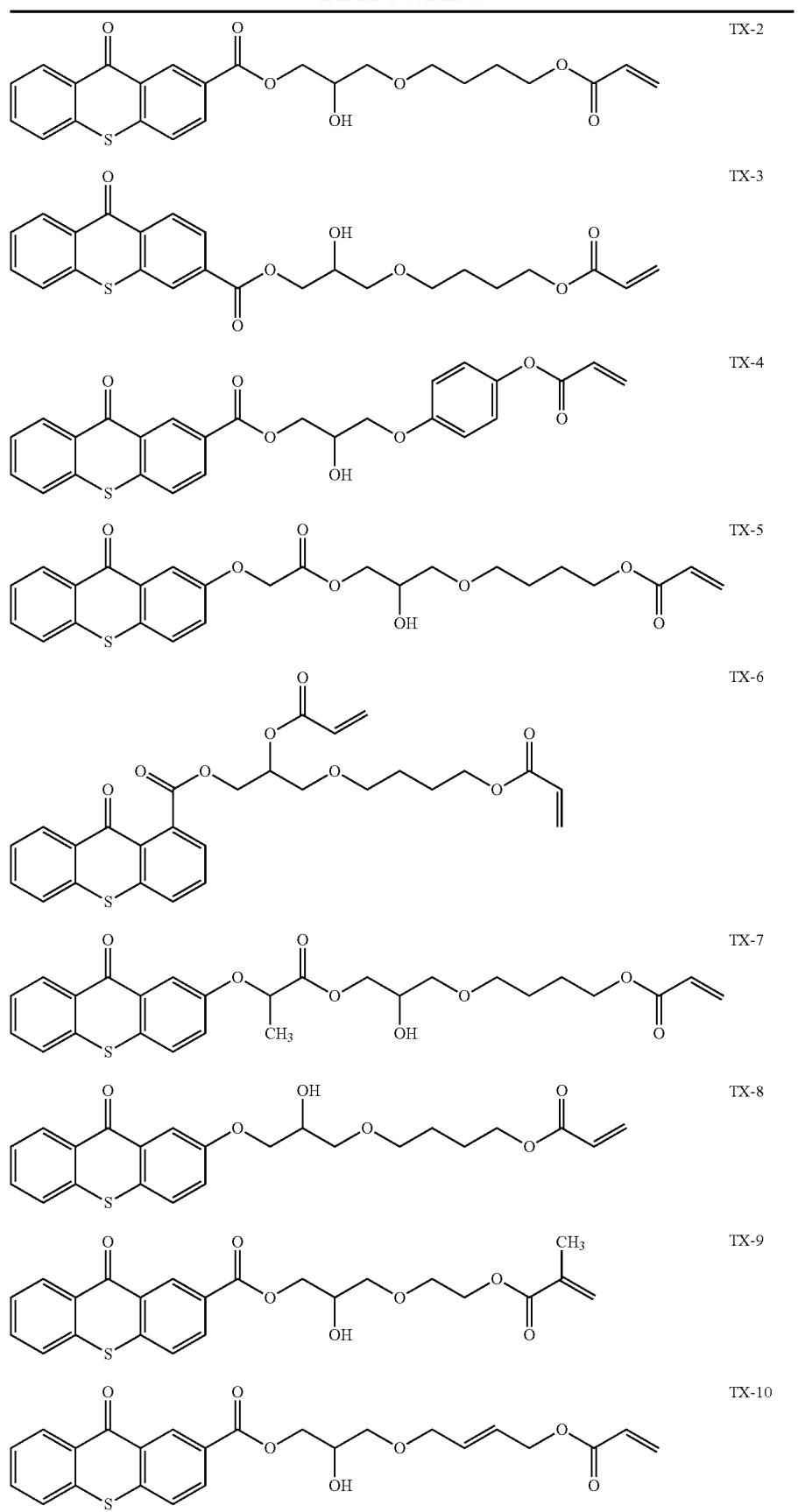

TABLE 1-continued
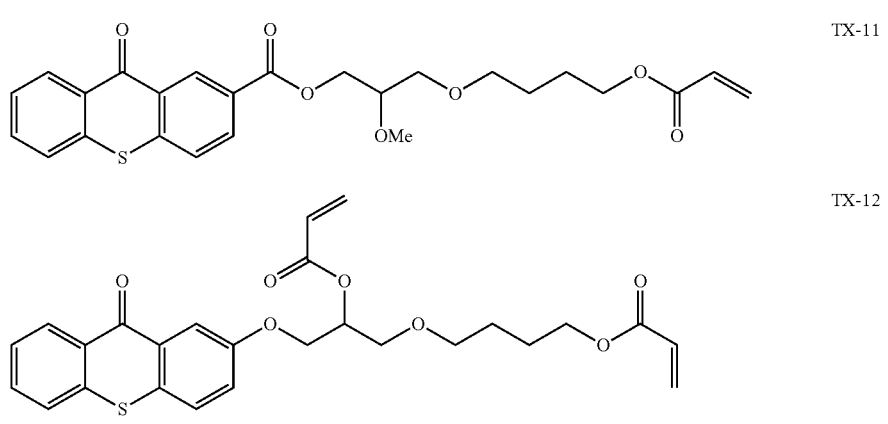
Preferred polymerizable Norrish Type II initiators containing a benzophenone group are given below in Table 2, without being limited thereto.
TABLE 2
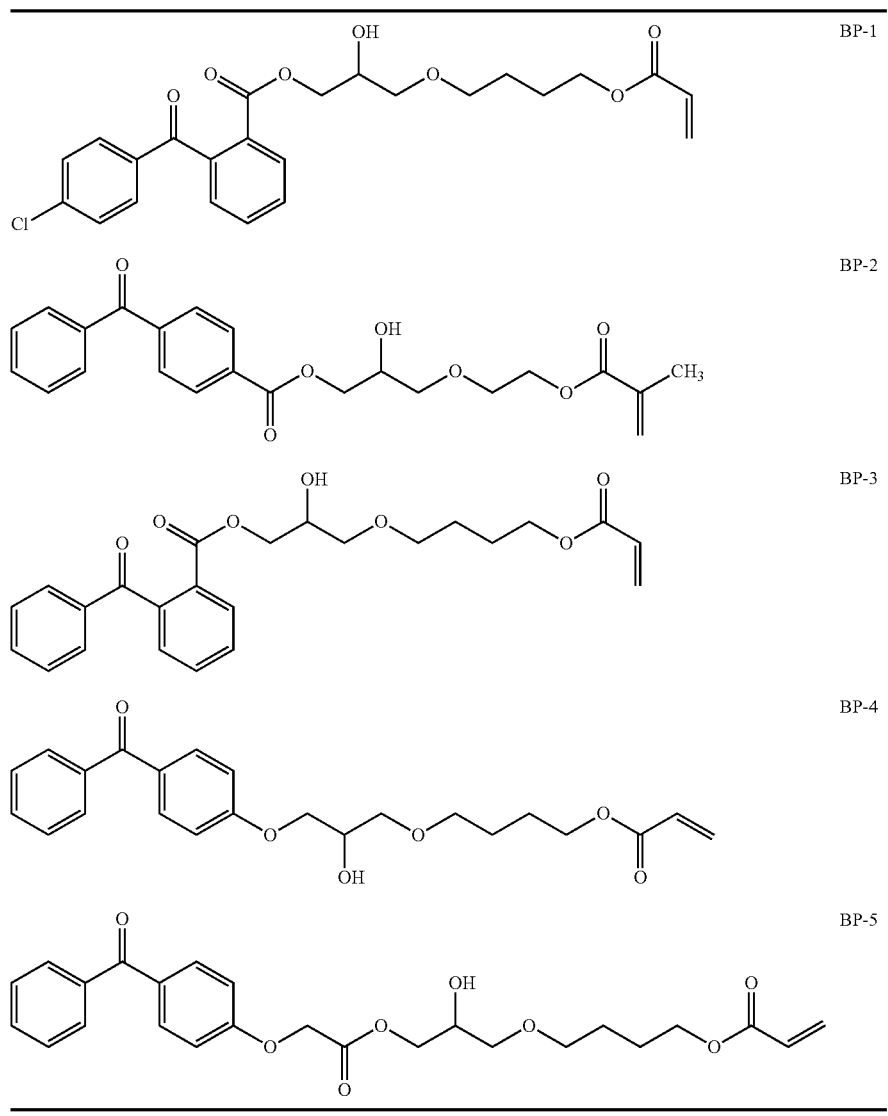

Radiation Curable Compositions and Inks

The radiation curable composition according to a preferred embodiment of the present invention includes the polymerizable Norrish Type II-photoinitiator as defined above and a co-initiator. A preferred amount of the polymerizable Norrish Type II-photoinitiator is 1 to 50 wt %, more preferably 2 to 25 wt %, and most preferably 5 to 10 wt % of the total weight of the radiation curable composition. Combinations of type I and type II photoinitiators can be used in the radiation curable compositions according to a preferred embodiment of the present invention.

In a most preferred embodiment the radiation curable composition includes one or more monomers and/or oligomers.

A preferred embodiment of radiation curable composition includes a polymerizable Norrish Type II-photoinitiator as defined above, a co-initiator and a polymerizable composition consisting essentially of:

a) 25-100 wt % of one or more polymerizable compounds PA having at least one acrylate group G1 and at least one second ethylenically unsaturated polymerizable functional group G2 selected from the group consisting of a vinylether group, an allylether group and a allylester group;

b) 0-55 wt % of one or more polymerizable compounds PB selected from the group consisting of monofunctional acrylates and difunctional acrylates; and c) 0-55 wt % of one or more polymerizable compounds PC selected from the group consisting of trifunctional acrylates, tetrafunctional acrylates, pentafunctional acrylates and hexafunctional acrylates, with the proviso that if the weight percentage of compounds PB>24 wt %, then the weight percentage of compounds PC>1 wt %;

and wherein all weight percentages of PA, PB and PC are based upon the total weight of the polymerizable composition.

Examples of the latter radiation curable compositions are disclosed in the unpublished EP 071191710 A (AGFA GRAPHICS), herein incorporated as a specific reference for the compounds PA, PB and PC, and for the polymerizable compositions of compounds PA, PB and PC.

The radiation curable compositions and inks are preferably cured by UV radiation and are preferably radiation curable inkjet liquids or inks. The radiation curable compositions and inks can also be advantageously used in offset printing, screen printing, flexographic printing and other printing or coating techniques.

The radiation curable compositions and inks are preferably non-aqueous liquids or inks. The term "non-aqueous" refers to a liquid carrier which should contain no water. However sometimes a small amount, generally less than 5 wt % of water based on the total weight of the composition or ink, can be present. This water was not intentionally added but came into the formulation via other components as a contamination, such as for example polar organic solvents. Higher amounts of water than 5 wt % tend to make the non-aqueous liquids and inks unstable, preferably the water content is less than 1 wt % based on the total weight of radiation curable composition or ink and most preferably no water at all is present.

The radiation curable compositions and inks preferably do not contain an evaporable component such as an organic solvent. But sometimes it can be advantageous to incorporate a small amount of an organic solvent to improve adhesion to the surface of a substrate after UV-curing. In this case, the added solvent can be any amount in the range that does not cause problems of solvent resistance and VOC, and preferably 0.1-10.0 wt %, and particularly preferably 0.1-5.0 wt %, each based on the total weight of the curable composition or ink.

The radiation curable compositions and inks are preferably part of an ink set, more preferably an inkjet ink set, comprising at least one ink containing one or more colorants, preferably one or more colour pigments. The curable ink set preferably comprises at least one yellow curable ink (Y), at least one cyan curable ink (C) and at least one magenta curable ink (M) and preferably also at least one black curable ink (K). The curable CMYK-ink set may also be extended with extra inks such as red, green, blue, and/or orange to further enlarge the colour gamut of the image. The CMYK-ink set may also be extended by the combination of full density and light density inks of both colour inks and/or black inks to improve the image quality by lowered graininess.

The pigmented radiation curable ink preferably contains a dispersant, more preferably a polymeric dispersant, for dispersing the pigment. The pigmented curable ink may contain a dispersion synergist to improve the dispersion quality and stability of the ink. Preferably, at least the magenta ink contains a dispersion synergist. A mixture of dispersion synergists may be used to further improve dispersion stability.

The viscosity of the curable liquid and ink is preferably smaller than 100 mPa·s at 30° C. and at a shear rate of 100 s$^{-1}$. The viscosity of the radiation curable inkjet inks and liquids is preferably smaller than 50 mPa·s, more preferably lower than 30 mPa·s, and most preferably between 2 and 15 mPa·s at a shear rate of 100 s$^{-1}$ and a jetting temperature between 10 and 70° C. In a more preferred embodiment, the viscosity of the radiation curable inkjet inks and liquids is preferably smaller than 50 mPa·s, more preferably lower than 30 mPa·s, and most preferably between 2 and 15 mPa·s at a shear rate of 100 s$^{-1}$ and a jetting temperature of 25° C.

The surface tension of the curable liquid and ink is preferably in the range of about 20 mN/m to about 70 mN/m at 25° C., more preferably in the range of about 22 mN/m to about 40 mN/m at 25° C.

The curable composition or ink may further also contain at least one inhibitor for improving the thermal stability of composition or ink The curable composition or ink may further also contain at least one surfactant for obtaining good spreading characteristics on a substrate.

Co-initiators

The radiation curable composition according to a preferred embodiment of the present invention contains at least one co-initiator, but may contain a mixture of 2, 3 or more co-initiators. A preferred amount of the co-initiator is 1 to 30 wt %, more preferably 2 to 20 wt %, and most preferably 5 to 10 wt % of the total weight of the radiation curable composition.

For safety reasons, in particular for food packaging applications, the radiation curable composition according to a preferred embodiment of the present invention contains at least one so-called diffusion hindered co-initiator. A diffusion hindered co-initiator is a co-initiator which exhibits a much lower mobility in a cured layer of the radiation curable composition or ink than a monofunctional, non-polymerizable co-initiator, such as a dialkylaminobenzoate. Several methods can be used to lower the mobility of the photoinitiator. One way is to increase the molecular weight of the co-initiator so that the diffusion speed is reduced, e.g. multifunctional co-initiators or polymeric co-initiators. Another way is to increase its reactivity so that it is built into the polymerizing network, e.g. multifunctional co-initiators and polymerizable co-initiators.

The diffusion hindered co-initiator is preferably selected from the group consisting of non-polymeric di- or multifunctional co-initiators, oligomeric or polymeric co-initiators and polymerizable co-initiators. Non-polymeric di- or multifunctional co-initiators usually have a molecular weight between 300 and 900 Dalton. Monofunctional co-initiators with a molecular weight in that range are not diffusion hindered co-initiators.

In a preferred embodiment of the radiation curable composition according to the present invention, the at least one co-initiator is a diffusion hindered dialkylamino substituted aromatic compound selected from the group consisting of an oligomeric or polymeric dialkylamino substituted aromatic compound, a multifunctional dialkylamino substituted aromatic compound and a dialkylamino substituted aromatic compound comprising at least one polymerizable ethylenically unsaturated group. A dialkylamino substituted aromatic compound comprising at least one polymerizable ethylenically unsaturated group is particularly preferred.

In a more preferred embodiment the dialkylamino substituted aromatic compound comprising at least one polymerizable ethylenically unsaturated group is a co-initiator according to Formula (III):

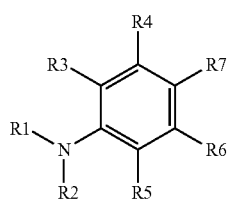

Formula (III)

wherein,

R1 and R2 are independently selected from the group consisting of an alkyl group, an alkenyl group, an alkynyl group, an aralkyl group, an alkaryl group, an aryl group and a heteroaryl group;

R3 to R6 are independently selected from the group consisting of hydrogen, an alkyl group, an alkenyl group, an alkynyl group, an acyl group, a thioalkyl group, an alkoxy group, a halogen, an aralkyl group, an alkaryl group, an aryl group and a heteroaryl group;

R7 is selected from the group consisting of hydrogen, an aldehyde group, a ketone group, an ester group, an amide group, an acyl group, a thioalkyl group, an alkoxy group, a halogen, a nitrile group, a sulphonate group, a sulphonamide group, an alkyl group, an alkenyl group, an alkynyl group, an aralkyl group, an alkaryl group, an aryl group and a heteroaryl group;

R1 and R2, R1 and R3, R2 and R5, R3 and R4, R4 and R7, R5 and R6, and R6 and R7 may represent the necessary atoms to form a 5- to 8-membered ring; and with the proviso that the aromatic amine has at least one α-hydrogen; and at least one of R1 to R7 comprises a polymerizable ethylenically unsaturated functional group selected from the group consisting of acrylate, substituted acrylate, methacrylate, styrene, acrylamide, methacrylamide, allyl ester, allyl ether, vinyl ester, vinyl ether, fumarate, maleate, maleimide and vinyl nitrile. In the polymerizable co-initiator, preferably R7 represents an electron withdrawing group selected from the group consisting of an aldehyde, a ketone, an ester and an amide, and more preferably R3, R4, R5 and R6 all represent hydrogen.

The alkyl groups, alkenyl groups, alkynyl groups, aralkyl groups, alkaryl groups, aryl groups and heteroaryl groups used for R1 to R7 can be substituted or unsubstituted groups, i.e. a substituted or unsubstituted alkyl group, a substituted or unsubstituted alkenyl group, a substituted or unsubstituted alkynyl group, a substituted or unsubstituted aralkyl group, a substituted or unsubstituted alkaryl group and a substituted or unsubstituted (hetero)aryl group may be used.

In a preferred embodiment, the polymerizable co-initiator corresponds to Formula (IV):

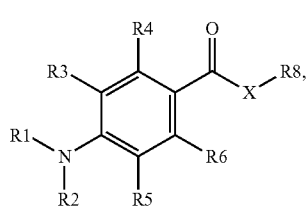

Formula (IV)

wherein,

R1 to R6 have the same meaning as defined for Formula (IV);

X is selected from the group consisting of O, S and NR9;

R8 and R9 are independently selected from the group consisting of hydrogen, an alkyl group, an alkenyl group, an alkynyl group, an aralkyl group, an alkaryl group, an aryl group and a heteroaryl group;

R1 and R2, R1 and R3, R2 and R5, R3 and R4, R5 and R6, R4 and R8, R6 and R8, and R8 and R9 may represent the necessary atoms to form a 5- to 8-membered ring; and at least one of R1 to R6 and R8 comprises a polymerizable ethylenically unsaturated functional group selected from the group consisting of acrylate, substituted acrylate, methacrylate, styrene, acrylamide, methacrylamide, allyl ester, allyl ether, vinyl ester, vinyl ether, fumarate, maleate, maleimide and vinyl nitrile. In the polymerizable co-initiator, preferably R3, R4, R5 and R6 all represent hydrogen.

In one preferred embodiment of the polymerizable co-initiator having Formula (IV), R1 represents methyl or ethyl and R2 comprises a polymerizable ethylenically unsaturated functional group selected from the group consisting of acrylate, substituted acrylate, methacrylate, styrene, acrylamide, methacrylamide, allyl ester, allyl ether, vinyl ester, vinyl ether, fumarate, maleate, maleimide and vinyl nitrile; and more preferably also R3, R4, R5 and R6 all represent hydrogen.

In another preferred embodiment of the polymerizable co-initiator having Formula (IV), R1 and R2 independently represent methyl or ethyl and R8 comprises a polymerizable ethylenically unsaturated functional group selected from the group consisting of acrylate, substituted acrylate, methacrylate, styrene, acrylamide, methacrylamide, allyl ester, allyl ether, vinyl ester, vinyl ether, fumarate, maleate, maleimide and vinyl nitrile; and more preferably also R3, R4, R5 and R6 all represent hydrogen.

In a more preferred embodiment, the polymerizable co-initiator corresponds to Formula (V):

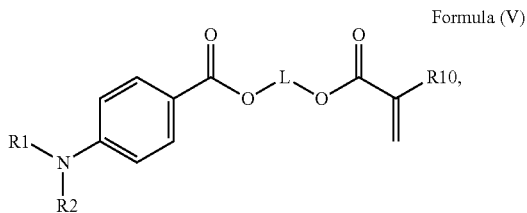

Formula (V)

wherein,
R1 and R2 are independently selected from the group consisting of methyl, ethyl, propyl and butyl;
L represents a divalent linking group comprising at least one carbon atom; and
R10 represents hydrogen, methyl, ethyl, propyl or butyl.

In a preferred embodiment of the polymerizable co-initiator corresponding to Formula (V), the divalent linking group L comprises 1 to 30 carbon atoms, more preferably 2 to 10 carbon atoms and most preferably 3 to 6 atoms.

The polymerizable co-initiator may contain two, three or more polymerizable ethylenically unsaturated functional groups independently selected from the group consisting of acrylate, substituted acrylate, methacrylate, styrene, acrylamide, methacrylamide, allyl ester, allyl ether, vinyl ester, vinyl ether, fumarate, maleate, maleimide and vinyl nitrile.

The polymerizable co-initiator may also contain more than one tertiary amine functional group, preferably the second or third tertiary amine functional group is also an aromatic tertiary amine, most preferably a dialkylamino benzoic acid derivative.

Examples of diffusion hindered co-initiators are given in Table 3 without being limited thereto. Suitable examples of oligomeric and polymeric dialkylamino substituted aromatic compounds are COINI-1 to COINI-3. Suitable examples of multifunctional dialkylamino substituted aromatic compounds are co-initiators COINI-4 to COINI-11. Suitable polymerizable co-initiators are co-initiators COINI-12 to COINI-26.

TABLE 3

COINI-1

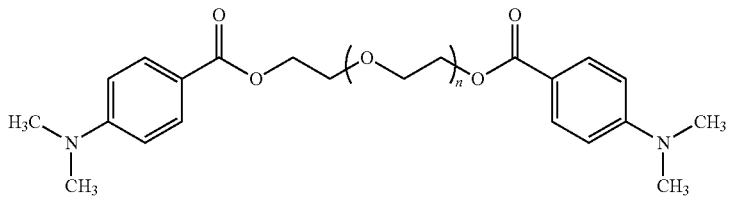

n = 13 on average

COINI-2

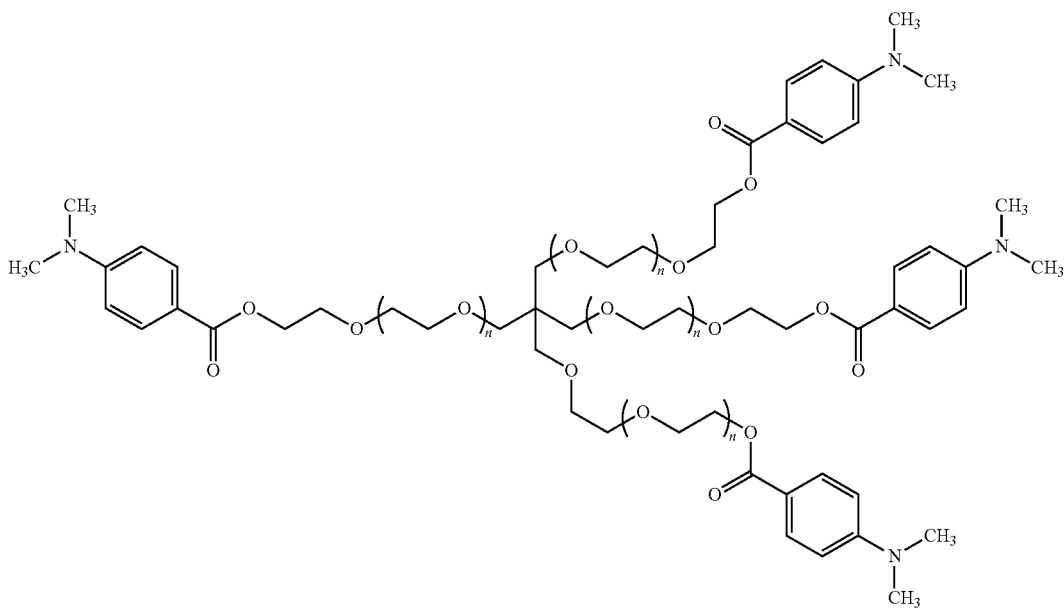

n = 3 on average

TABLE 3-continued
COINI-3
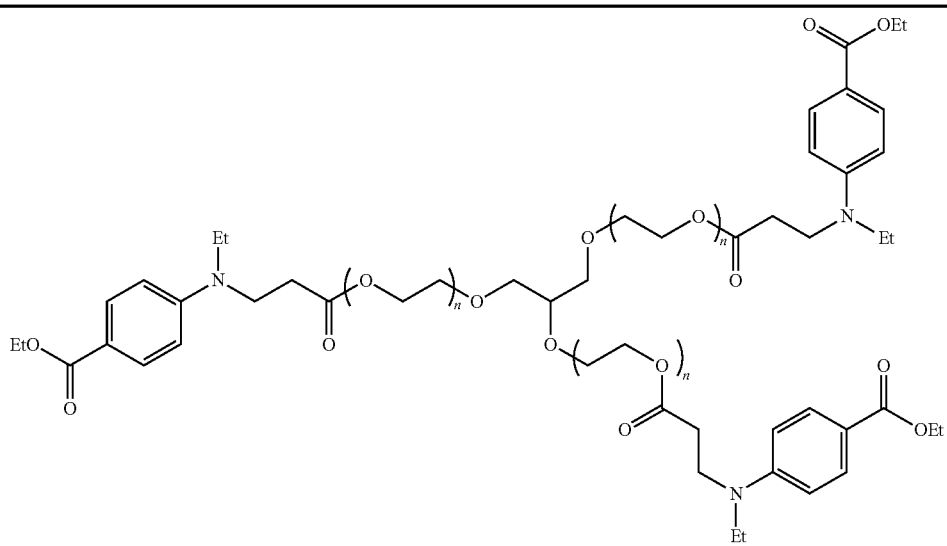
COINI-4
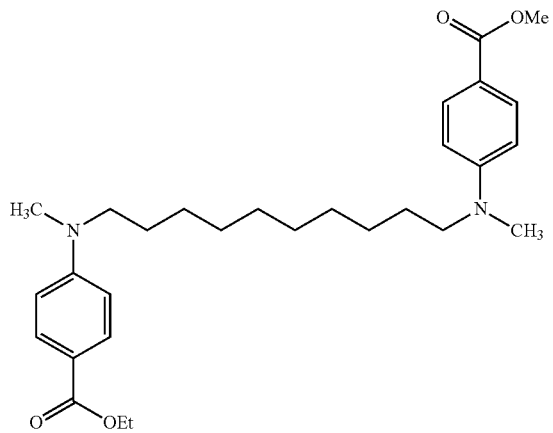 [SMILES: CCOC(=O)c1ccc(N(C)CCCCCCCCCCN(C)c2ccc(C(=O)OC)cc2)cc1]
COINI-5
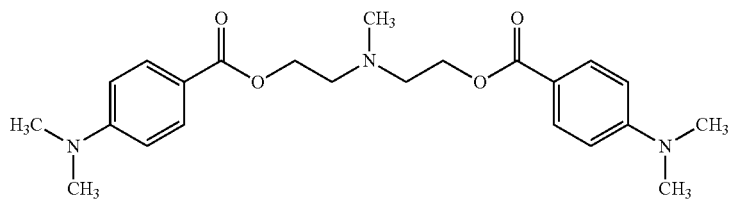
COINI-6
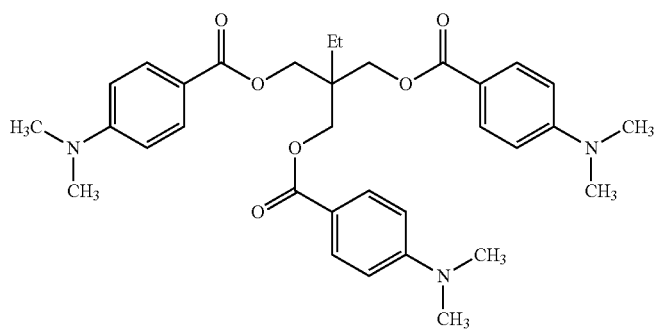

TABLE 3-continued
COINI-7
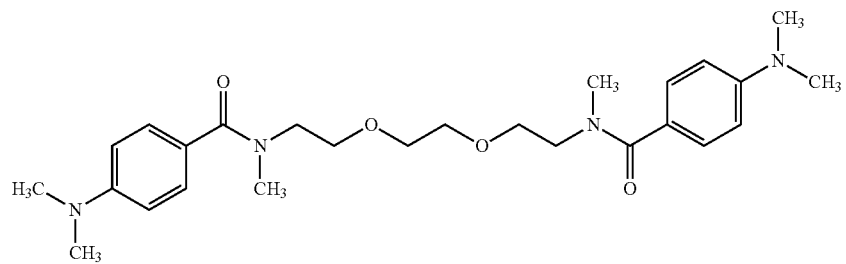
COINI-8
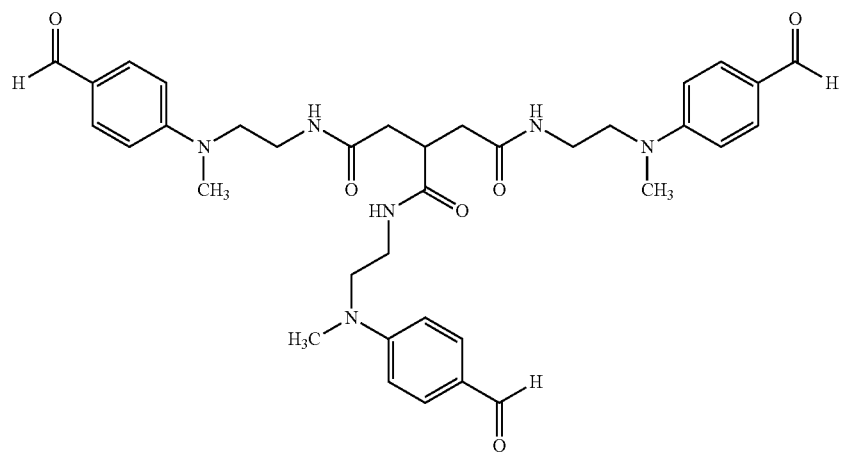 [SMILES: CN(CCNC(=O)CC(CC(=O)NCCN(C)c1ccc(C=O)cc1)C(=O)NCCN(C)c1ccc(C=O)cc1)c1ccc(C=O)cc1]
COINI-9
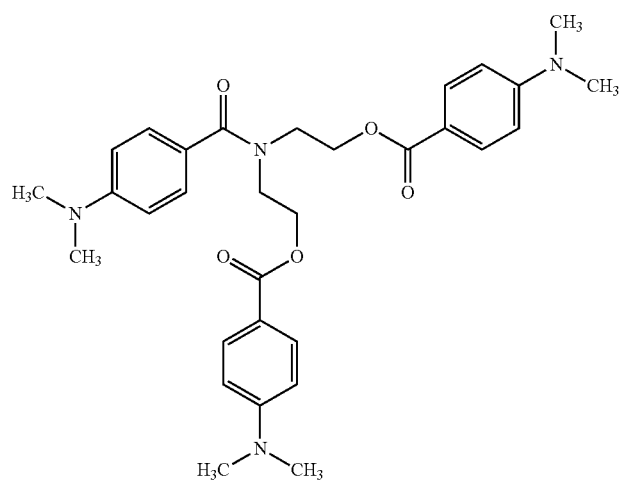
COINI-10
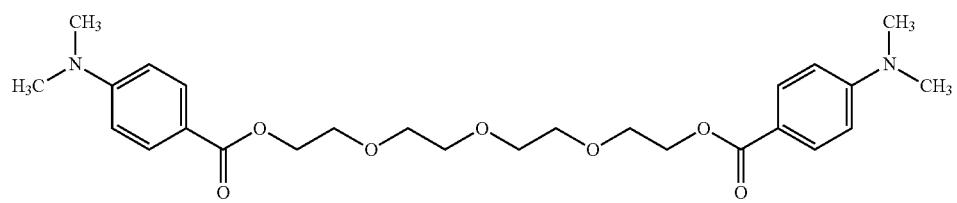
COINI-11
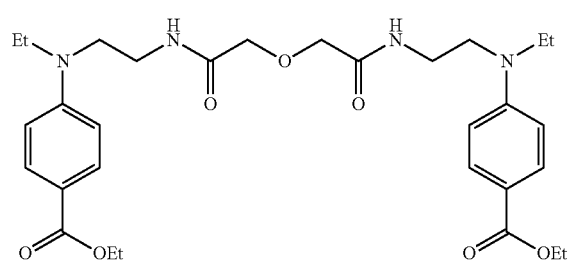 [SMILES: CCOC(=O)c1ccc(N(CC)CCNC(=O)COCC(=O)NCCN(CC)c2ccc(C(=O)OCC)cc2)cc1]

TABLE 3-continued
COINI-12
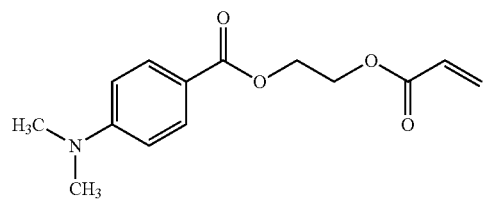 [SMILES: C=CC(=O)OCCOC(=O)c1ccc(N(C)C)cc1]
COINI-13
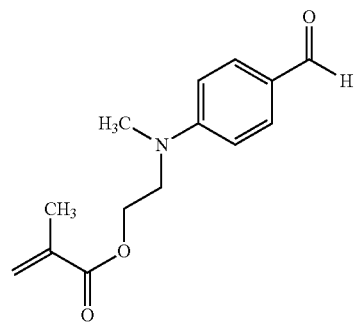 [SMILES: C=C(C)C(=O)OCCN(C)c1ccc(C=O)cc1]
COINI-14
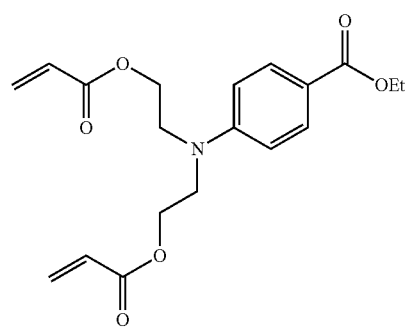 [SMILES: C=CC(=O)OCCN(CCOC(=O)C=C)c1ccc(C(=O)OCC)cc1]
COINI-15
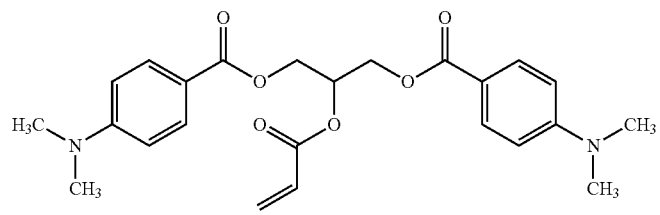
COINI-16
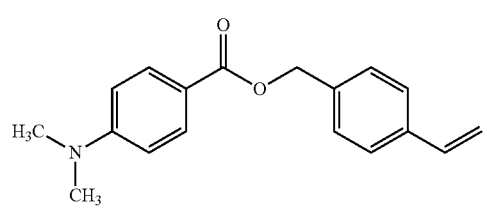 [SMILES: C=Cc1ccc(COC(=O)c2ccc(N(C)C)cc2)cc1]
COINI-17
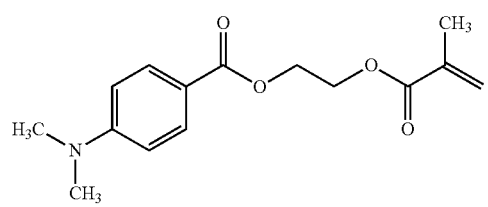 [SMILES: C=C(C)C(=O)OCCOC(=O)c1ccc(N(C)C)cc1]

TABLE 3-continued
COINI-18
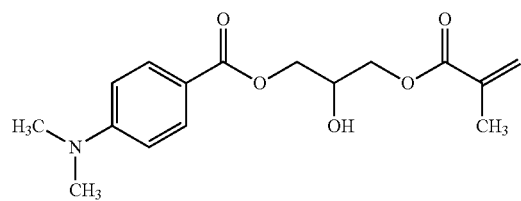 [SMILES: C=C(C)C(=O)OCC(O)COC(=O)c1ccc(N(C)C)cc1]
COINI-19
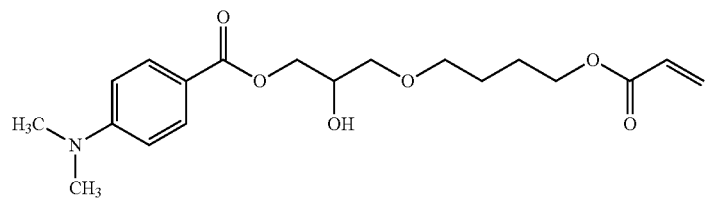 [SMILES: C=CC(=O)OCCCCOCC(O)COC(=O)c1ccc(N(C)C)cc1]
COINI-20
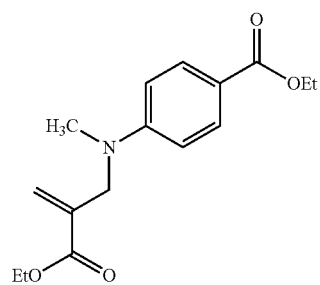 [SMILES: C=C(CN(C)c1ccc(C(=O)OCC)cc1)C(=O)OCC]
COINI-21
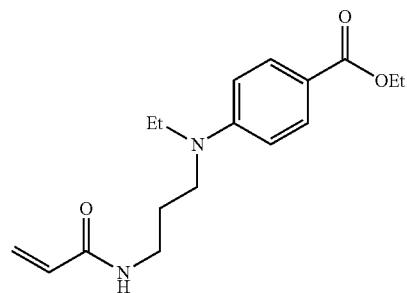 [SMILES: C=CC(=O)NCCCN(CC)c1ccc(C(=O)OCC)cc1]
COINI-22
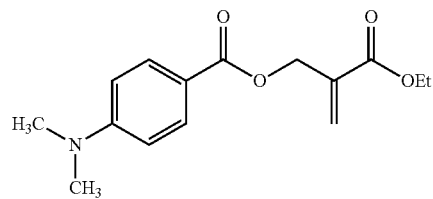 [SMILES: C=C(COC(=O)c1ccc(N(C)C)cc1)C(=O)OCC]
COINI-23
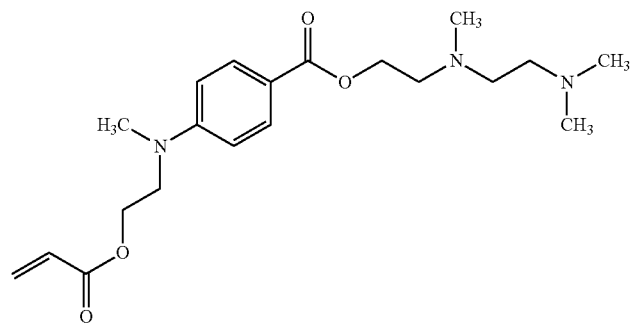 [SMILES: C=CC(=O)OCCN(C)c1ccc(C(=O)OCCN(C)CCN(C)C)cc1]

TABLE 3-continued

COINI-24

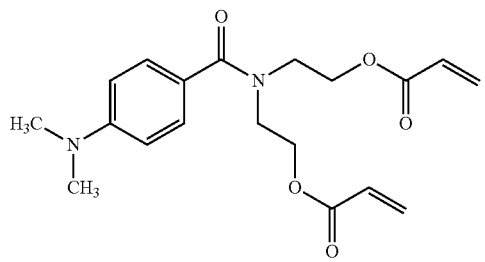 [SMILES: C=CC(=O)OCCN(CCOC(=O)C=C)C(=O)c1ccc(N(C)C)cc1]

COINI-25

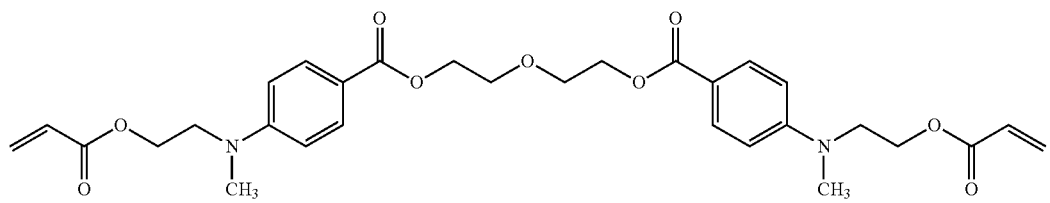 [SMILES: C=CC(=O)OCCN(C)c1ccc(C(=O)OCCOCCOC(=O)c2ccc(N(C)CCOC(=O)C=C)cc2)cc1]

COINI-26

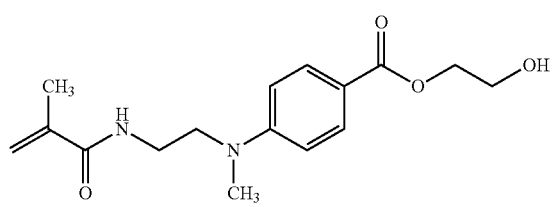 [SMILES: C=C(C)C(=O)NCCN(C)c1ccc(C(=O)OCCO)cc1]

Monomers and Oligomers

The monomers and oligomers used in the radiation curable compositions and inks, especially for food packaging applications, are preferably purified compounds having no or almost no impurities, more particularly no toxic or carcinogenic impurities. The impurities are usually derivative compounds obtained during synthesis of the polymerizable compound. Sometimes, however, some compounds may be added deliberately to pure polymerizable compounds in harmless amounts, for example, polymerization inhibitors or stabilizers.

Any monomer or oligomer capable of free radical polymerization may be used as polymerizable compound. A combination of monomers, oligomers and/or prepolymers may also be used. The monomers, oligomers and/or prepolymers may possess different degrees of functionality, and a mixture including combinations of mono-, di-, tri- and higher functionality monomers, oligomers and/or prepolymers may be used. The viscosity of the radiation curable compositions and inks can be adjusted by varying the ratio between the monomers and oligomers.

Particularly preferred monomers and oligomers are those listed in [0106] to [0115] in EP 1911814 A (AGFA GRAPHICS) incorporated herein as a specific reference.

A preferred class of monomers and oligomers are vinyl ether acrylates such as those described in U.S. Pat. No. 6,310,115 (AGFA), incorporated herein by reference. Particularly preferred compounds are 2-(2-vinyloxyethoxy)ethyl (meth) acrylate, most preferably the compound is 2-(2-vinyloxyethoxy)ethyl acrylate.

Inhibitors

The radiation curable compositions and inks may contain a polymerization inhibitor. Suitable polymerization inhibitors include phenol type antioxidants, hindered amine light stabilizers, phosphor type antioxidants, hydroquinone monomethyl ether commonly used in (meth)acrylate monomers, and hydroquinone, t-butylcatechol, pyrogallol, 2,6-di-tert.butyl-4-methylphenol may also be used.

Suitable commercial inhibitors are, for example, SUMILIZER™ GA-80, SUMILIZER™ GM and SUMILIZER™ GS produced by Sumitomo Chemical Co. Ltd.; GENORAD™16, GENORAD™18 and GENORAD™20 from Rahn AG; IRGASTAB™ UV10 and IRGASTAB™ UV22, TINUVIN™460 and CGS20 from Ciba Specialty Chemicals; FLOORSTAB™ UV range (UV-1, UV-2, UV-5 and UV-8) from Kromachem Ltd, ADDITOL™ S range (S100, S110, S120 and S130) from Cytec Surface Specialties.

The inhibitor is preferably a polymerizable inhibitor.

Since excessive addition of these polymerization inhibitors may lower the curing speed, it is preferred that the amount capable of preventing polymerization is determined prior to blending. The amount of a polymerization inhibitor is preferably lower than 5 wt %, more preferably lower than 3 wt % of the total ink or liquid.

Surfactants

The radiation curable compositions and inks may contain a surfactant. The surfactant(s) can be anionic, cationic, nonionic, or zwitter-ionic and are usually added in a total quantity less than 10 wt % based on the total weight of the radiation curable compositions or ink and particularly in a total less than 5 wt % based on the total weight of the radiation curable composition or ink.

Suitable surfactants include those disclosed in paragraphs [0283] to [0291] of WO 2008/074548 (AGFA GRAPHICS) incorporated herein as a specific reference.

Colorants

Colorants used in the radiation curable inks may be dyes, pigments or a combination thereof. Organic and/or inorganic pigments may be used. The colorant is preferably a pigment or a polymeric dye, most preferably a pigment.

The pigments may be black, white, cyan, magenta, yellow, red, orange, violet, blue, green, brown, mixtures thereof, and the like. This colour pigment may be chosen from those disclosed by HERBST, Willy, et al. Industrial Organic Pigments, Production, Properties, Applications. 3rd edition. Wiley—VCH, 2004. ISBN 3527305769.

Suitable pigments are disclosed in paragraphs [0128] to [0138] of WO 2008/074548 (AGFA GRAPHICS).

Suitable pigments include mixed crystals of the above particular preferred pigments. Mixed crystals are also referred to as solid solutions. For example, under certain conditions different quinacridones mix with each other to form solid solutions, which are quite different from both physical mixtures of the compounds and from the compounds themselves. In a solid solution, the molecules of the components enter into the same crystal lattice, usually, but not always, that of one of the components. The x-ray diffraction pattern of the resulting crystalline solid is characteristic of that solid and can be clearly differentiated from the pattern of a physical mixture of the same components in the same proportion. In such physical mixtures, the x-ray pattern of each of the components can be distinguished, and the disappearance of many of these lines is one of the criteria of the formation of solid solutions. A commercially available example is Cinquasia Magenta RT-355-D from Ciba Specialty Chemicals.

Also mixtures of pigments may be used in the radiation curable inks. For some inkjet applications, a neutral black inkjet ink is preferred and can be obtained, for example, by mixing a black pigment and a cyan pigment into the ink. The inkjet application may also require one or more spot colours, for example for packaging inkjet printing or textile inkjet printing. Silver and gold are often desired colours for inkjet poster printing and point-of-sales displays.

Non-organic pigments may be used in the colour inkjet inks. Particular preferred pigments are C.I. Pigment Metal 1, 2 and 3. Illustrative examples of the inorganic pigments include red iron oxide (III), cadmium red, ultramarine blue, prussian blue, chromium oxide green, cobalt green, amber, titanium black and synthetic iron black.

Pigment particles in inkjet inks should be sufficiently small to permit free flow of the ink through the inkjet-printing device, especially at the ejecting nozzles. It is also desirable to use small particles for maximum colour strength and to slow down sedimentation.

The numeric average pigment particle size is preferably between 0.050 and 1 µm, more preferably between 0.070 and 0.300 µm and particularly preferably between 0.080 and 0.200 µm. Most preferably, the numeric average pigment particle size is no larger than 0.150 µm. An average particle size smaller than 0.050 µm is less desirable for decreased light-fastness, but mainly also because very small pigment particles or individual pigment molecules thereof may still be extracted in food packaging applications. The average particle size of pigment particles is determined with a Brookhaven Instruments Particle Sizer BI90plus based upon the principle of dynamic light scattering. The ink is diluted with ethyl acetate to a pigment concentration of 0.002 wt %. The measurement settings of the BI90plus are: 5 runs at 23° C., angle of 90°, wavelength of 635 nm and graphics=correction function.

However for a white radiation curable ink, the numeric average particle diameter of the white pigment is preferably from 50 to 500 nm, more preferably from 150 to 400 nm, and most preferably from 200 to 350 nm. Sufficient hiding power cannot be obtained when the average diameter is less than 50 nm, and the storage ability and the jet-out suitability of the ink tend to be degraded when the average diameter exceeds 500 nm. The determination of the numeric average particle diameter is best performed by photon correlation spectroscopy at a wavelength of 633 nm with a 4 mW HeNe laser on a diluted sample of the pigmented inkjet ink. A suitable particle size analyzer used was a MALVERN™ nano-S available from Goffin-Meyvis. A sample can be, for example, be prepared by addition of one drop of ink to a cuvet containing 1.5 mL ethyl acetate and mixed until a homogenous sample was obtained. The measured particle size is the average value of 3 consecutive measurements consisting of 6 runs of 20 seconds.

Suitable white pigments are given by Table 2 in [0116] of WO 2008/074548 (AGFA GRAPHICS). The white pigment is preferably a pigment with a refractive index greater than 1.60. The white pigments may be employed singly or in combination. Preferably titanium dioxide is used as pigment with a refractive index greater than 1.60. Suitable titanium dioxide pigments are those disclosed in [0117] and in [0118] of WO 2008/074548 (AGFA GRAPHICS).

The pigments are present in the range of 0.01 to 10% by weight, preferably in the range of 0.1 to 5% by weight, each based on the total weight of radiation curable ink. For white radiation curable inks, the white pigment is preferably present in an amount of 3% to 30% by weight of the ink composition, and more preferably 5% to 25%. An amount of less than 3% by weight cannot achieve sufficient covering power and usually exhibits very poor storage stability and ejection property.

Generally pigments are stabilized in the dispersion medium by dispersing agents, such as polymeric dispersants. However, the surface of the pigments can be modified to obtain so-called "self-dispersible" or "self-dispersing" pigments, i.e. pigments that are dispersible in the dispersion medium without dispersants.

Dispersants

The dispersant is preferably a polymeric dispersant. Typical polymeric dispersants are copolymers of two monomers but may contain three, four, five or even more monomers. The properties of polymeric dispersants depend on both the nature of the monomers and their distribution in the polymer. Suitable copolymeric dispersants have the following polymer compositions:

statistically polymerized monomers (e.g. monomers A and B polymerized into ABBAABAB);
alternating polymerized monomers (e.g. monomers A and B polymerized into ABABABAB);
gradient (tapered) polymerized monomers (e.g. monomers A and B polymerized into AAABAABBABBB);
block copolymers (e.g. monomers A and B polymerized into AAAAABBBBBB) wherein the block length of each of the blocks (2, 3, 4, 5 or even more) is important for the dispersion capability of the polymeric dispersant;
graft copolymers (graft copolymers consist of a polymeric backbone with polymeric side chains attached to the backbone); and
mixed forms of these polymers, e.g. blocky gradient copolymers.

Suitable polymeric dispersants are listed in the section on "Dispersants", more specifically [0064] to [0070] and [0074] to [0077], in EP 1911814 A (AGFA GRAPHICS) incorporated herein as a specific reference.

The polymeric dispersant has preferably a number average molecular weight Mn between 500 and 30,000, more preferably between 1,500 and 10,000.

The polymeric dispersant has preferably a weight average molecular weight Mw smaller than 100,000, more preferably smaller than 50000 and most preferably smaller than 30,000.

The polymeric dispersant has preferably a polydispersity PD smaller than 2, more preferably smaller than 1.75 and most preferably smaller than 1.5.

Commercial examples of polymeric dispersants are the following:

- DISPERBYK™ dispersants available from BYK CHEMIE GMBH;
- SOLSPERSE™ dispersants available from NOVEON;
- TEGO™ DISPERS™ dispersants from DEGUSSA;
- EDAPLAN™ dispersants from MÜNZING CHEMIE;
- ETHACRYL™ dispersants from LYONDELL;
- GANEX™ dispersants from ISP;
- DISPEX™ and EFKA™ dispersants from CIBA SPECIALTY CHEMICALS INC;
- DISPONER™ dispersants from DEUCHEM; and
- JONCRYL™ dispersants from JOHNSON POLYMER.

Particularly preferred polymeric dispersants include SOLSPERSE™ dispersants from NOVEON, EFKA™ dispersants from CIBA SPECIALTY CHEMICALS INC and DISPERBYK™ dispersants from BYK CHEMIE GMBH. Particularly preferred dispersants are SOLSPERSE™ 32000, 35000 and 39000 dispersants from NOVEON.

The polymeric dispersant is preferably used in an amount of 2 to 600 wt %, more preferably 5 to 200 wt % based on the weight of the pigment.

Dispersion Synergists

A dispersion synergist usually consists of an anionic part and a cationic part. The anionic part of the dispersion synergist exhibiting a certain molecular similarity with the colour pigment and the cationic part of the dispersion synergist consists of one or more protons and/or cations to compensate the charge of the anionic part of the dispersion synergist.

The synergist is preferably added in a smaller amount than the polymeric dispersant(s). The ratio of polymeric dispersant/dispersion synergist depends upon the pigment and should be determined experimentally. Typically the ratio wt % polymeric dispersant/wt % dispersion synergist is selected between 2:1 to 100:1, preferably between 2:1 and 20:1.

Suitable dispersion synergists that are commercially available include SOLSPERSE™ 5000 and SOLSPERSE™ 22000 from NOVEON.

Particular preferred pigments for the magenta ink used are a diketopyrrolo-pyrrole pigment or a quinacridone pigment. Suitable dispersion synergists include those disclosed in EP 1790698 A (AGFA GRAPHICS), EP 1790696 A (AGFA GRAPHICS), WO 2007/060255 (AGFA GRAPHICS) and EP 1790695 A (AGFA GRAPHICS).

In dispersing C.I. Pigment Blue 15:3, the use of a sulfonated Cu-phthalocyanine dispersion synergist, e.g. SOLSPERSE™ 5000 from NOVEON is preferred. Suitable dispersion synergists for yellow inkjet inks include those disclosed in EP 1790697 A (AGFA GRAPHICS).

Preparation of Radiation Curable Inks

The average particle size and distribution is an important feature for inkjet inks. The ink may be prepared by precipitating or milling the pigment in the dispersion medium in the presence of the dispersant.

Mixing apparatuses may include a pressure kneader, an open kneader, a planetary mixer, a dissolver, and a Dalton Universal Mixer. Suitable milling and dispersion apparatuses are a ball mill, a pearl mill, a colloid mill, a high-speed disperser, double rollers, a bead mill, a paint conditioner, and triple rollers. The dispersions may also be prepared using ultrasonic energy.

Many different types of materials may be used as milling media, such as glasses, ceramics, metals, and plastics. In a preferred embodiment, the grinding media can comprise particles, preferably substantially spherical in shape, e.g. beads consisting essentially of a polymeric resin or yttrium stabilized zirconium oxide beads.

In the process of mixing, milling and dispersion, each process is performed with cooling to prevent build up of heat, and for radiation curable inks as much as possible under light conditions in which actinic radiation has been substantially excluded.

The ink may contain more than one pigment, the ink may be prepared using separate dispersions for each pigment, or alternatively several pigments may be mixed and co-milled in preparing the dispersion.

The dispersion process can be carried out in a continuous, batch or semi-batch mode.

The preferred amounts and ratios of the ingredients of the mill grind will vary widely depending upon the specific materials and the intended applications. The contents of the milling mixture comprise the mill grind and the milling media. The mill grind comprises pigment, polymeric dispersant and a liquid carrier. For inkjet inks, the pigment is usually present in the mill grind at 1 to 50 wt %, excluding the milling media. The weight ratio of pigment over polymeric dispersant is 20:1 to 1:2.

The milling time can vary widely and depends upon the pigment, selected mechanical devices and residence conditions, the initial and desired final particle size, etc. In a preferred embodiment of the present invention pigment dispersions with an average particle size of less than 100 nm may be prepared.

After milling is completed, the milling media is separated from the milled particulate product (in either a dry or liquid dispersion form) using conventional separation techniques, such as by filtration, sieving through a mesh screen, and the like. Often the sieve is built into the mill, e.g. for a bead mill. The milled pigment concentrate is preferably separated from the milling media by filtration.

In general it is desirable to make the inks in the form of a concentrated mill grind, which is subsequently diluted to the appropriate concentration for use in the printing system. This technique permits preparation of a greater quantity of pigmented ink from the equipment. By dilution, the ink is adjusted to the desired viscosity, surface tension, colour, hue, saturation density, and print area coverage for the particular application.

Inkjet Printing Methods

The inkjet printing method according to a preferred embodiment of the present invention comprises the steps of:
a) providing a radiation curable composition according to a preferred embodiment of the present invention; and
b) at least partially curing the radiation curable composition.

In a preferred embodiment of the inkjet printing method according to the present invention, the radiation curable composition is applied to a substrate by inkjet printing or by flexographic printing. For example, the radiation curable composition is applied as a primer on a substrate by flexographic printing and at least partially cured, and then a solvent inkjet ink or radiation curable inkjet ink is printed on the at least partially cured primer.

In one embodiment of the inkjet printing method, the applied layer is a white primer, preferably containing a titanium dioxide pigment. White primers can be advantageously used, for example, on transparent substrates to enhance the contrast and the vividness of colour inks. White curable inks are then either used for so-called "surface printing" or "backing printing" to form a reflection image on a transparent substrate. In surface printing, a white background is formed on a transparent substrate using a white ink and further thereon, a colour image is printed, where after the formed final image is viewed from the printed face. In so-called backing printing, a colour image is formed on a transparent substrate using colour inks and then a white ink is applied onto the colour inks, and the final formed image is observed through the transparent substrate. In a preferred embodiment a colour inkjet ink is jetted on partially cured white inkjet ink. If the white ink is only partially cured, an improved wettability of the colour ink on the white ink layer is observed. Partially curing immobilizes the ink on the substrate surface. A quick test to verify that the white inkjet ink is partially cured can be done by rubbing a finger or a cloth across the printed surface, whereby it is observed that ink can be smeared or smudged on the surface.

In another preferred embodiment of the inkjet printing method, the applied layer is a colourless layer. This layer can be present as a primer, for example, for improving the adhesion of the image, or as an outermost layer, for example, for improving the glossiness of the image.

The above layers are preferably applied by a printing technique selected from the group consisting of inkjet printing, flexographic printing, offset printing and screen printing.

Alternatively, above layers are applied by a coating technique selected from the group consisting of dip coating, knife coating, extrusion coating, spin coating, slide hopper coating and curtain coating.

Inkjet Printing Device

Curable compositions and inks according to a preferred embodiment of the present invention may be jetted by one or more print heads ejecting small droplets of ink in a controlled manner through nozzles onto an ink-receiver surface, which is moving relative to the print head(s).

A preferred print head for the inkjet printing system is a piezoelectric head. Piezoelectric inkjet printing is based on the movement of a piezoelectric ceramic transducer when a voltage is applied thereto. The application of a voltage changes the shape of the piezoelectric ceramic transducer in the print head creating a void, which is then filled with ink. When the voltage is again removed, the ceramic expands to its original shape, ejecting a drop of ink from the print head. However the inkjet printing method according to the present invention is not restricted to piezoelectric inkjet printing. Other inkjet print heads can be used and include various types, such as a continuous type and thermal, electrostatic and acoustic drop on demand type.

At high printing speeds, the inks must be ejected readily from the print heads, which puts a number of constraints on the physical properties of the ink, e.g. a low viscosity at the jetting temperature, which may vary from 25° C. to 110° C., a surface energy such that the print head nozzle can form the necessary small droplets, a homogenous ink capable of rapid conversion to a dry printed area, . . .

The inkjet print head normally scans back and forth in a transversal direction across the moving ink-receiver surface. Often the inkjet print head does not print on the way back. Bi-directional printing is preferred for obtaining a high areal throughput. Another preferred printing method is by a "single pass printing process", which can be performed by using page wide inkjet print heads or multiple staggered inkjet print heads which cover the entire width of the ink-receiver surface. In a single pass printing process the inkjet print heads usually remain stationary and the ink-receiver surface is transported under the inkjet print heads.

Curing Device

Curable compositions and inks according to a preferred embodiment of the present invention can be cured by exposing them to actinic radiation, preferably by ultraviolet radiation.

The curing device may be arranged in combination with the print head of the inkjet printer, travelling therewith so that the curable composition is exposed to curing radiation very shortly after been jetted.

In such an arrangement it can be difficult to provide a small enough radiation source connected to and travelling with the print head. Therefore, a static fixed radiation source may be employed, e.g. a source of curing UV-light, connected to the radiation source by means of flexible radiation conductor such as a fibre optic bundle or an internally reflective flexible tube.

Alternatively, the actinic radiation may be supplied from a fixed source to the radiation head by an arrangement of mirrors including a mirror upon the radiation head.

The source of radiation arranged not to move with the print head, may also be an elongated radiation source extending transversely across the ink-receiver surface to be cured and adjacent the transverse path of the print head so that the subsequent rows of images formed by the print head are passed, stepwise or continually, beneath that radiation source.

Any ultraviolet light source, as long as part of the emitted light can be absorbed by the photo-initiator or photo-initiator system, may be employed as a radiation source, such as, a high or low pressure mercury lamp, a cold cathode tube, a black light, an ultraviolet LED, an ultraviolet laser, and a flash light. Of these, the preferred source is one exhibiting a relatively long wavelength UV-contribution having a dominant wavelength of 300-400 nm. Specifically, a UV-A light source is preferred due to the reduced light scattering therewith resulting in more efficient interior curing.

UV radiation is generally classed as UV-A, UV-B, and UV-C as follows:

UV-A: 400 nm to 320 nm

UV-B: 320 nm to 290 nm

UV-C: 290 nm to 100 nm.

Furthermore, it is possible to cure the image using, consecutively or simultaneously, two light sources of differing wavelength or illuminance. For example, the first UV-source can be selected to be rich in UV-C, in particular in the range of 260 nm-200 nm. The second UV-source can then be rich in UV-A, e.g. a gallium-doped lamp, or a different lamp high in both UV-A and UV-B. The use of two UV-sources has been found to have advantages e.g. a fast curing speed and a high curing degree.

For facilitating curing, the inkjet printer often includes one or more oxygen depletion units. The oxygen depletion units place a blanket of nitrogen or other relatively inert gas (e.g. $CO_2$), with adjustable position and adjustable inert gas concentration, in order to reduce the oxygen concentration in the curing environment. Residual oxygen levels are usually maintained as low as 200 ppm, but are generally in the range of 200 ppm to 1200 ppm.

EXAMPLES

Materials

All materials used in the following examples were readily available from standard sources such as Aldrich Chemical Co. (Belgium) and Acros (Belgium) unless otherwise specified. The water used was deionized water.

VEEA is 2-(vinylethoxy)ethyl acrylate, a difunctional monomer available from NIPPON SHOKUBAI, Japan:

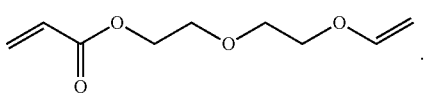

M600 is dipentaerythritol hexaacrylate and an abbreviation for MIRAMER™ M600 available from RAHN AG.

IC127 is IRGACURE™127 is 2-hydroxy-1-{4-[4-(2-hydroxy-2-methyl-propionyl)-benzyl]-phenyl}-2-methyl-propan-1-one, a photoinitiator available from CIBA SPECIALTY CHEMICALS.

Type I is an α-hydroxy-ketone Norrish Type I photoinitiator, having the following structure:

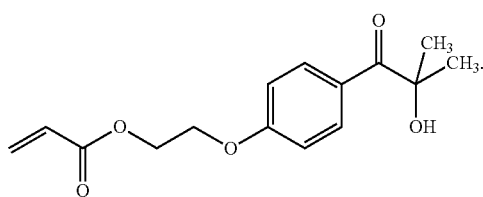 [SMILES: C=CC(=O)OCCOc1ccc(C(=O)C(C)(C)O)cc1]

COINI-1 is GENOPOL™ AB, a polymeric aminobenzoate derivate supplied by RAHN AG.

COINI-2 is a polymerizable coïnitiator, having the following structure:

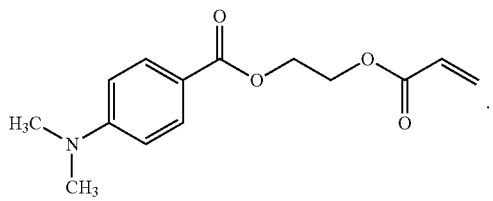 [SMILES: C=CC(=O)OCCOC(=O)c1ccc(N(C)C)cc1]

TEGO™ Rad 2100 is a silicone polyether acrylate surfactant available from DEGUSSA.

PET100 is a 100 μm unsubbed PET substrate with on the backside an antiblocking layer with antistatic properties available from AGFA-GEVAERT as P100C PLAIN/ABAS.

Measurement

1. Curing Degree

The curing degree is tested on a coating immediately after curing with UV light. The cured coating is rubbed with the means of a Qtip. When the surface is not damaged, the coating is fully cured. When some of the cured coating can be damaged, the coating is only partly cured. When the whole cured coating is damaged, the coating is not cured.

2. Curing Speed

The curing speed was defined as the percentage of the maximum output of the lamp needed to cure the samples. The lower the number the higher curing speed. A sample was considered as fully cured at the moment scratching with a Q-tip caused no visual damage.

A percentage of more then 100% of the maximum output of the lamp means that the speed of the conveyer belt had to be reduced to get the sample fully cured at the maximum output of the lamp. The higher the percentage, the more the belt had to be slowed down. A curing speed of 160% means a belt speed of 12.5 m/min at the maximum output of the lamp. A percentage between 150% and 200% is considered as at the edge of practical use. A percentage above 200% is considered out of the range for practical use and no higher percentages are measured.

3. Viscosity

The viscosity of the formulations was measured using a Brookfield DV-II+ viscometer at 25° C. at 3 rotations per minute (RPM) using a CPE 40 spindle. A viscosity of less than 50 mPa·s was regarded to be suitable for inkjet printing.

Example 1

This example illustrates the synthesis of polymerizable Norrish Type II photoinitiators according to a preferred embodiment of the present invention.

Synthesis of precursor
9-oxo-9H-thioxanthen-1-carboxylic acid

The synthesis of 9-oxo-9H-thioxanthen-1-carboxylic acid was optimized starting from the synthesis, disclosed in U.S. Pat. No. 4,367,324 (CIBA-GEIGY).

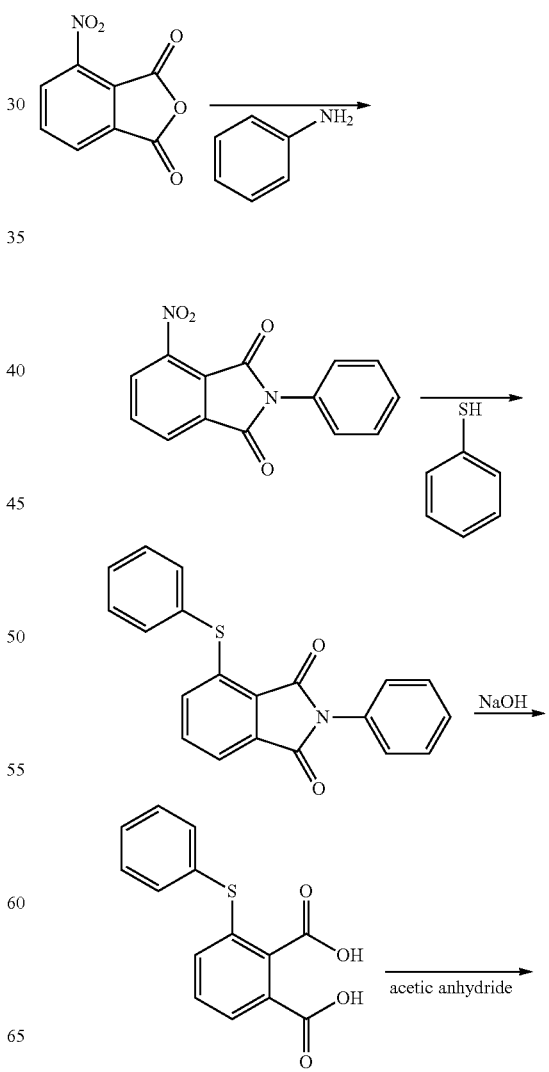

-continued

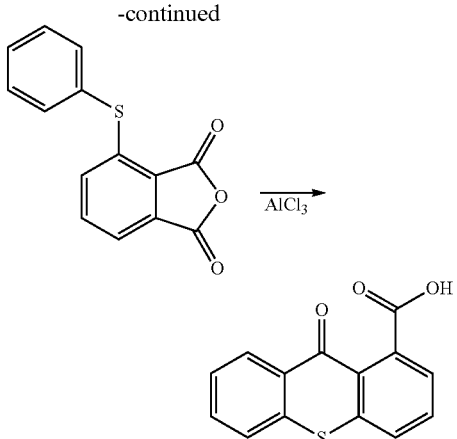

3-nitro-phtalanilide 50 g (259 mmol) 3-nitro-phtalic anhydride and 24.7 g (24.1 mL, 266 mmol) aniline in 710 mL acetic acid were heated to reflux for 3 hours under an argon atmosphere. Acetic acid was removed under reduced pressure and the residue was treated with 150 mL ethanol at 0° C. The precipitated 3-nitro-phtalanilide was isolated by filtration, washed with a small amount of cold ethanol and dried. 59.1 g (58%) 3-nitro-phtanilide was isolated (m.p. 139-141° C.).

3-phenylthio-phtalanilide 22.2 mL (204 mmol) thiophenol was added to a sodium methanolate solution, freshly prepared from 4.63 g (204 mmol) sodium in 185 mL methanol. The solvent was removed under reduced pressure and the isolated sodium thiophenolate was dissolved in 185 mL DMSO. 49.7 g (185 mmol) 3-nitro-phtalanilide was added and the mixture was heated, while stirring, to 50° C. for 90 minutes. The mixture was added carefully to a mixture of 185 mL acetic acid and 185 mL water, while stirring to suppress foaming. The precipitated 3-phenylthio-phtalanilide was isolated by filtration, washed with water at 0° C. and dried under reduced pressure at 85° C. 60.5 g (99%) of 3-phenylthio-phtalanilide was isolated (m.p. 150-2° C.).

3-phenylthio-phtalic acid 34.33 g (103.6 mmol) 3-phenylthio-phtalanilide was suspended in 466 mL of a 20% sodium hydroxide solution. The mixture was heated for 30 minutes to 105° C. (severe foaming!). The mixture was allowed to cool down to room temperature and carefully poured into 239 mL concentrated hydrochloric acid, while cooling. The crude 3-phenylthio-phtalic acid was isolated by filtration, suspended in 330 mL concentrated hydrochloric acid, heated to reflux and allowed to cool down. 3-phenylthio-phtalic acid was isolated by filtration, washed twice with 2 N hydrochloric acid, then twice with a saturated NaCl-solution and dried under reduced pressure at 85° C. 26.7 g (94%) of 3-phenylthio-phtalic acid was isolated (m.p. 154-8° C.).

3-phenylthio-phtalic anhydride 25.6 g (93.5 mmol) 3-phenylthio-phtalic acid and 26.4 mL (281 mmol) acetic anhydride were heated to reflux for 6 hours. The reaction mixture was allowed to cool down to room temperature. Upon standing over night, 3-phenylthio-phtalic anhydride precipitated from the medium. A first crop of 16.8 g of 3-phenylthio-phtalic anhydride was isolated by filtration and dried. The filtrate was evaporated to half of its volume and a second crop of 4.1 g of 3-phenylthio-phtalic anhydride was isolated. 20.9 g (87%) of 3-phenylthio-phtalic anhydride was isolated (m.p. 148-50° C.)

9-oxo-9H-thioxanthen-1-carboxylic acid 17.5 g (68.3 mmol) 3-phenylthio-phtalic anhydride was suspended in 170 mL toluene. 9.64 g (72.8 mmol) AlCl$_3$ was added and the reaction was allowed to continue for 4 hours at room temperature. Toluene was decanted and the residue was treated with water at 0° C. 9-oxo-9H-thioxanthen-1-carboxylic acid precipitated from the medium, was isolated by filtration, washed with water and dried. 15.7 g (90%) of the crude 9-oxo-9H-thioxanthen-1-carboxylic acid was isolated (m.p. 269-70° C.). The carboxylic acid was used without further purification.

Synthesis of precursor
9-oxo-9H-thioxanthene-2-carboxylic acid

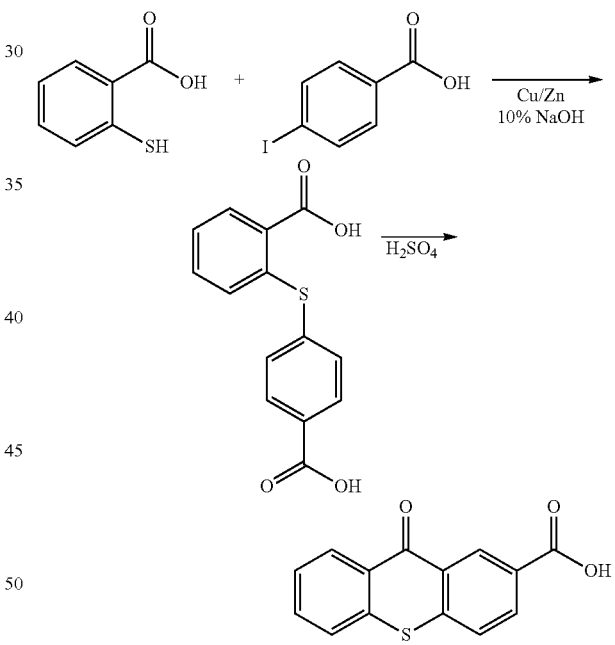

diphenylsulfide-2,4'-dicarboxylic acid 31.08 g (202 mmol) thiosalicylic acid and 50 g (202 mmol) 4-iodo-benzoic acid were added to 410 mL of 10% NaOH. 12.3 g copper powder and 2.04 g zinc powder were added and the mixture was refluxed for 6 hours, while vigorously stirring. The foaming was difficult to control. The reaction mixture was allowed to cool down to room temperature. The copper and zinc powder were removed by filtration. The reaction mixture was diluted with 800 mL water and neutralized with 600 mL 2N HCl. The precipitated diphenylsulfide-2,4'-dicarboxylic acid was isolated by filtration washed three times with water and dried. 55 g of diphenylsulfide-2,4'-dicarboxylic acid was isolated. (m.p. 235-7° C.)

9-oxo-9H-thioxanthene-2-carboxylic acid 52.74 (192 mmol) diphenylsulfide-2,4'-dicarboxylic acid was dissolved in 1 L concentrated sulfuric acid and the reaction was allowed to continue for 24 hours at room temperature. The reaction mixture was added slowly to 12 L boiling water. The mixture was kept at 100° C. for an additional hour. The mixture was allowed to cool down to room temperature. The crude 9-oxo-9H-thioxanthene-2-carboxylic acid precipitated from the mixture, was isolated by filtration, washed three times with water and once with ethanol and dried. 41.76 g of the crude 9-oxo-9H-thioxanthene-2-carboxylic acid was dissolved in 417 mL 2N NaOH, stirred for 30 minutes at room temperature and slowly acidified with 600 ml 2N HCl. The mixture was stirred for 30 minutes and the precipitated 9-oxo-9H-thioxanthene-2-carboxylic acid was isolated by filtration, washed twice with water and twice with ethanol and dried. 31.5 g (64%) 9-oxo-9H-thioxanthene-2-carboxylic acid was isolated (m.p.: 310-6° C.).

Synthesis of TX-1

Synthesis of 9-oxo-9H-thioxanthene-1-carboxylic acid-3-(4-acryloyloxy-butoxy)-2-hydroxy-propyl ester

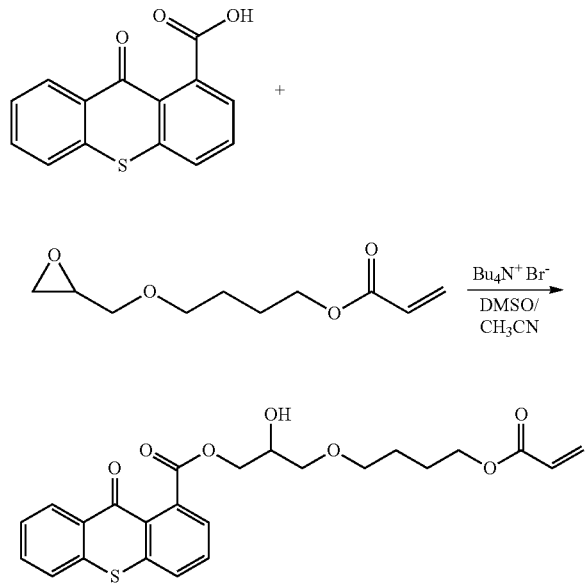

A reaction mixture containing 9-oxo-9H-thioxanthene-1-carboxylic acid (3.8 g, 15 mmol), acetonitrile (40 mL), dimethylsulfoxide (23 mL), tetrabutylammonium bromide (0.5 g, 1.5 mmol) and 2,6-di-tert-butyl-4-methylphenol (0.03 g, 0.122 mmol) was heated to reflux.

At this temperature 4-hydroxybutylacrylate glycidylether (2.4 g, 12.2 mmol) was added and the mixture was allowed to stir at reflux temperature for 24 hours.

The mixture was cooled to room temperature and filtered to remove the residual, undissolved 9-oxo-9H-thioxanthene-1-carboxylic acid. The filtrate was evaporated under reduced pressure.

The residual oil, which contains dimethylsulfoxide, was brought in distilled water. After stirring for 1 hour the aqueous layer was decanted off. The residue was dissolved in dichloromethane (100 mL) and extracted with a mixture of an aqueous solution of sodium hydroxide (1N) and distilled water (1/2).

The organic layer was separated, dried on MgSO$_4$, filtered and evaporated to provide 4.9 g of a yellow oil.

The product was purified on a SVP D40 Merck Np Column using dichloromethane/ethyl acetate (80/20) as eluent, to afford 2.6 g of a yellow oil.

Synthesis of TX-2

Synthesis of 9-oxo-9H-thioxanthene-2-carboxylic acid-3-(4-acryloyloxy-butoxy)-2-hydroxy-propyl ester

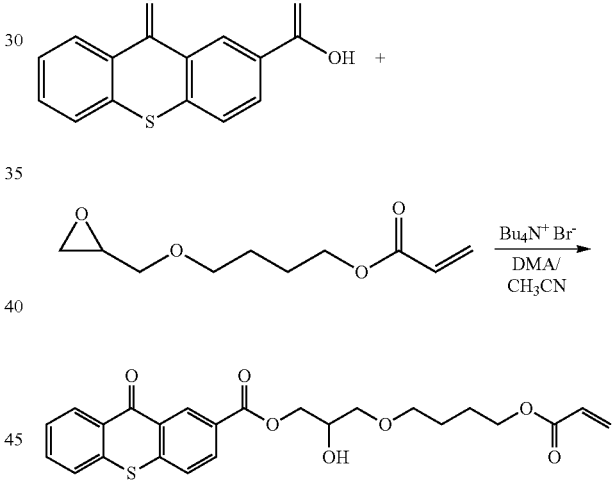

A reaction mixture containing 9-oxo-9H-thioxanthene-2-carboxylic acid (2.0 g, 7.8 mmol), acetonitrile (30 mL), dimethylacetamide (20 mL), tetrabutylammonium bromide (0.3 g, 0.78 mmol) and 2,6-di-tert-butyl-4-methylphenol (0.02 g, 0.0634 mmol) was heated to reflux.

At this temperature 4-hydroxybutylacrylate glycidylether (1.3 g, 6.34 mmol) was added and the mixture was allowed to stir at reflux temperature for 24 hours.

The mixture was cooled to room temperature and filtered to remove the residual, undissolved 9-oxo-9H-thioxanthene-2-carboxylic acid. The filtrate was evaporated under reduced pressure.

The residual oil was dissolved in methyl-tert-butylether (100 mL) and extracted with a mixture of an aqueous solution of sodium hydroxide (1N) and distilled water (1/4).

The organic layer was separated, dried on MgSO$_4$, filtered and evaporated to provide 2.5 g of a brown oil.

Synthesis of TX-7

Synthesis of acrylic acid 4-{2-hydroxy-3-[2-(9-oxo-9H-thioxanthen-2-yloxy)-propionyloxy]propoxy}-butyl ester

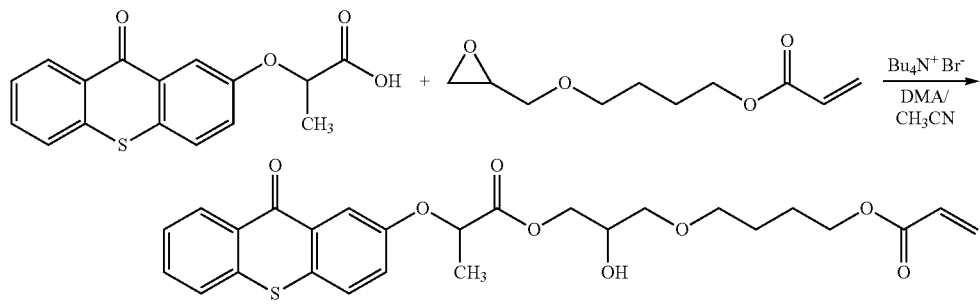

2-[(9-oxo-9H-thioxanthen-2-yl)oxy]-propionic acid was prepared according to EP 1380580 A (GREAT LAKES).

A reaction mixture containing 2-(9-oxo-9H-thioxanthene-2-yloxy)-propionic acid (4.2 g, 14 mmol), acetonitrile (55 mL), dimethylacetamide (10 mL), tetrabutylammonium bromide (0.5 g, 1.4 mmol) and 2,6-di-tert-butyl-4-methylphenol (0.03 g, 0.114 mmol) was heated to reflux.

At this temperature 4-hydroxybutylacrylate glycidylether (2.3 g, 11.4 mmol) was added and the mixture was allowed to stir at reflux temperature for 16 hours.

The mixture was cooled to room temperature and the solvent was evaporated under reduced pressure.

The residual oil was dissolved in methyl-tert-butylether (100 mL) and extracted with a mixture of an aqueous solution of sodium hydroxide (1N) and distilled water (1/1).

The organic layer was separated, dried on MgSO$_4$, filtered and evaporated to provide 3.7 g of a yellow oil.

Synthesis of TX-5

Synthesis of acrylic acid 4-{2-hydroxy-3-[2-(9-oxo-9H-thioxanthen-2-yloxy)-acetoxy]-propoxy}-butyl ester

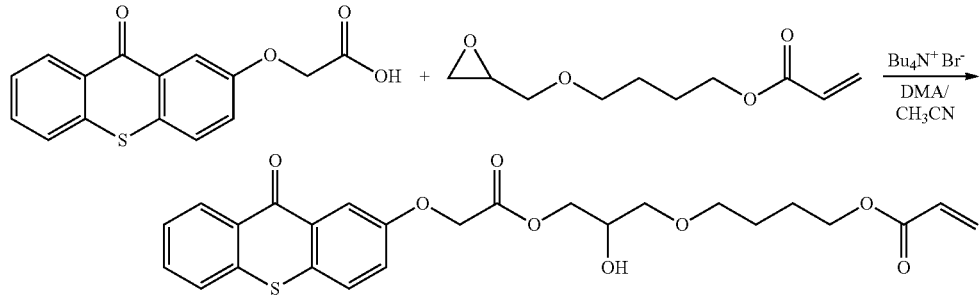

2-[(9-oxo-9H-thioxanthen-2-yl)oxy]-acetic acid was prepared according to EP 1380580 A (GREAT LAKES).

A reaction mixture containing (9-oxo-9H-thioxanthen-2-yloxy)acetic acid (4.0 g, 14 mmol), acetonitrile (55 ml), dimethylacetamide (10 mL), tetrabutylammonium bromide (0.5 g, 1.4 mmol) and 2,6-di-tert-butyl-4-methylphenol (0.03 g, 0.114 mmol) was heated to reflux. At this temperature 4-hydroxybutylacrylate glycidylether (2.3 g, 11.4 mmol) was added and the mixture was allowed to stir at reflux temperature for 16 hours. The mixture was cooled to room temperature and the solvent was evaporated under reduced pressure to provide 8.0 g of a yellow oil. The product was purified on a Prochrom LC80 Column using dichloromethane/ethyl acetate (60/40) as eluent on Kromasil Si60A 10 μm, to afford 1.8 g of a yellow oil.

Synthesis of BP-3

Synthesis of 2-benzoyl-benzoic acid 3-(4-acryloyloxy-butoxy)-2-hydroxy-propylester

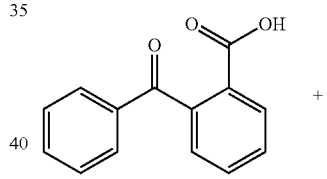

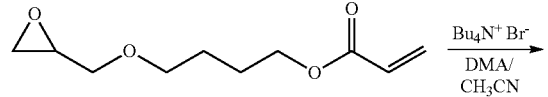

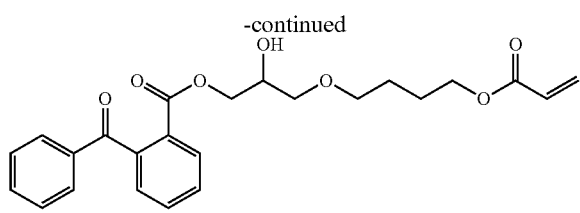

A reaction mixture containing 2-benzoyl benzoic acid (40.0 g), acetonitrile (300 mL), dimethylacetamide (10 mL), tetrabutylammonium bromide (5.6 g) and 2,6-di-tert-butyl-4-methylphenol (0.3 g) was heated to reflux.

At this temperature 4-hydroxybutylacrylate glycidylether (28.0 g) was added and the mixture was allowed to stir at reflux temperature for 16 hours. The mixture was cooled to room temperature and the solvent was evaporated under reduced pressure. The residual oil was dissolved in methyl-tert-butylether (300 mL) and extracted 3 times with a mixture of an aqueous solution of sodium hydroxide (1N) and distilled water (1/2.4) The organic layer was separated, dried on $MgSO_4$, filtered and evaporated to provide 45.2 g of a brown oil.

Synthesis of BP-4

Synthesis of Acrylic acid 4-[3-(4-benzoyl-phenoxy)-2-hydroxy-propoxy]butyl ester

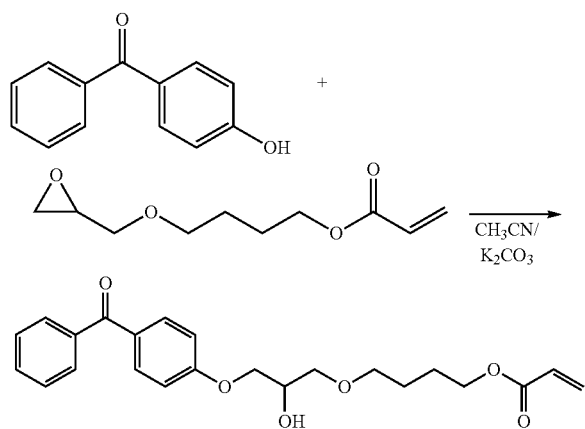

A reaction mixture containing 4-hydroxybenzophenone (14.9 g, 75 mmol), acetonitrile (40 mL), potassium carbonate (7.8 g, 56.3 mmol) and 4-hydroxybutylacrylate glycidylether (7.5 g, 37.5 mmol) was heated to reflux. The mixture was allowed to stir at reflux temperature for 24 hours. The mixture was cooled to room temperature and filtered to remove the undissolved potassium carbonate. The filtrate was evaporated under reduced pressure. The residual oil was diluted with ethyl acetate (250 ml) and extracted with a mixture of an aqueous solution of sodium hydroxide (1N) and distilled water (4/1). The organic layer was separated, dried over $MgSO_4$, filtered and evaporated to provide 15.1 g of a yellow oil. The product was purified on a SVP D40 Merck Np Column using dichloromethane/n-hexane (50/50) as eluent, to afford 5.5 g of a yellow oil.

Example 2

This example illustrates that the polymerizable Norrish Type II photoinitiators according to a preferred embodiment of the present invention have an improved compatibility with radiation curable compositions in comparison to two comparative polymerizable Norrish Type II photoinitiators COMPINI-1 and COMPINI-2.

Synthesis of Comparative Initiator COMPINI-1

The comparative initiator COMPINI-1 is 9-oxo-9H-thioxanthen-1-carboxylic acid-(2-acryloyloxyethyl ester).

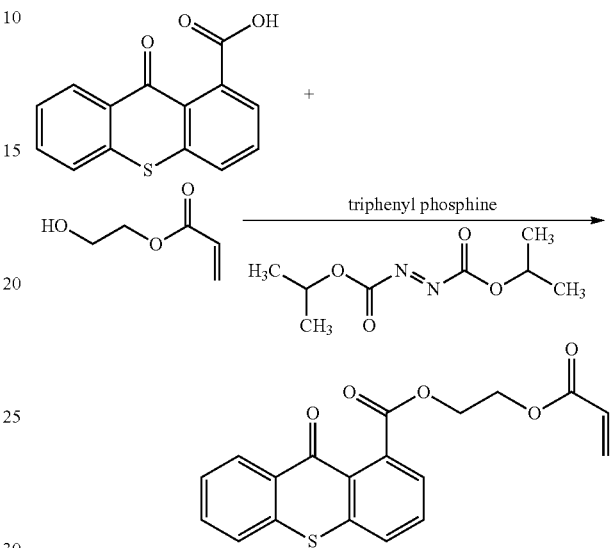

10 g (39 mmol) 9-oxo-9H-thioxanthen-1-carboxylic acid, 33.2 g (128 mmol) triphenyl phosphine and 14.8 g (13.4 mL, 128 mmol) 2-hydroxyethyl acrylate were dissolved in 100 mL dimethyl formamide. 28 mL (128 mmol) di-isopropyl-azodicarboxylate was added drop wise. During the addition, the temperature rose to 80° C. The reaction was allowed to continue for 48 hours at room temperature. The solvent was removed under reduced pressure at 45° C. The residue was treated with water and extracted three times with 200 mL chloroform. The precipitated triphenyl phosphine oxide was removed by filtration and the pooled chloroform fractions were extracted twice with 200 mL water. The organic fraction was dried over $MgSO_4$ and evaporated under reduced pressure. The excess of reaction products were removed by preparative chromatography on Kieselgel 60, using cyclohexane/ethyl acetate 1/1 as eluent. The pooled fractions containing 9-oxo-9H-thioxanthen-1-carboxylic acid-(2-acryloyloxyethyl ester) were evaporated under reduced pressure and the residue was treated with 50 mL ethanol. 9-oxo-9H-thioxanthen-1-carboxylic acid-(2-acryloyloxyethyl ester) was isolated by filtration, washed with ethanol and dried. 3.0 g (22%) of 9-oxo-9H-thioxanthen-1-carboxylic acid-(2-acryloyloxyethyl ester) was isolated (m.p. 118-9° C.).

Synthesis of Comparative Initiator COMPINI-2

The comparative initiator COMPINI-2 is 2-propenoic acid-(9-oxo-9H-thioxanthen-2-yl ester).

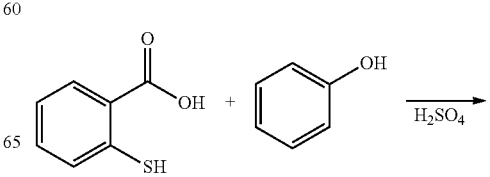

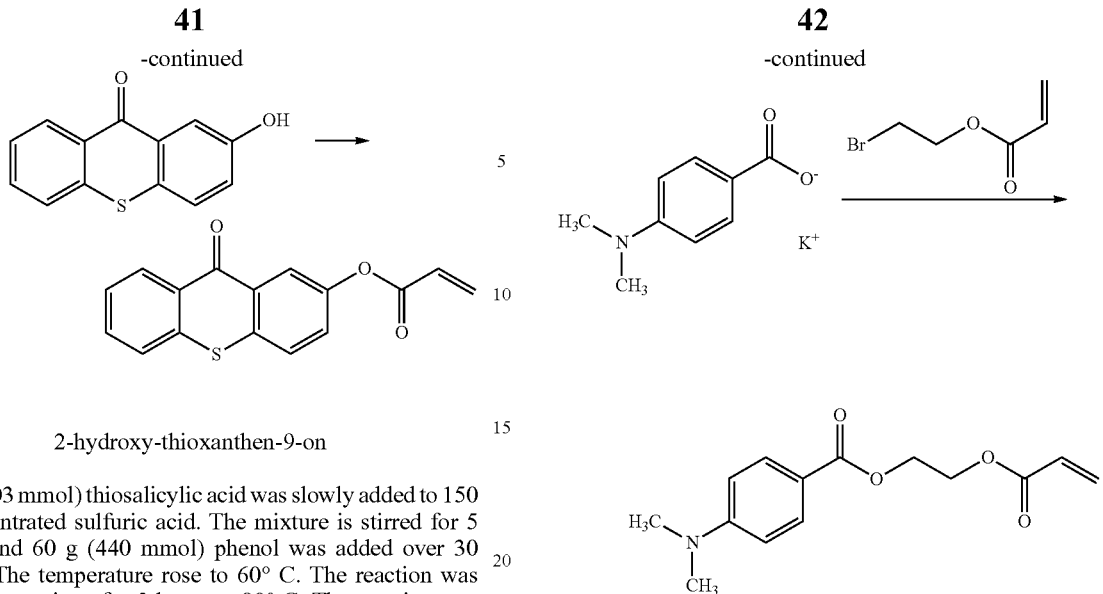

2-hydroxy-thioxanthen-9-on 16 g (103 mmol) thiosalicylic acid was slowly added to 150 mL concentrated sulfuric acid. The mixture is stirred for 5 minutes and 60 g (440 mmol) phenol was added over 30 minutes. The temperature rose to 60° C. The reaction was allowed to continue for 2 hours at 80° C. The reaction was allowed to cool down to room temperature and was added slowly to 3 l boiling water. The mixture was kept at the boiling point for 5 minutes. The mixture was allowed to cool down to room temperature. The precipitated 2-hydroxy-thioxanthen-9-on was isolated by filtration and dried. 14.1 g (63%) of 2-hydroxy-thioxanthen-9-on was isolated (m.p. 232-241° C.).

2-Propenoic acid-(9-oxo-9H-thioxanthen-2-yl ester)

30 g (130 mmol) 2-hydroxy-thioxanthen-9-on was suspended in 300 mL acetone. 63.5 g (460 mmol) potassium carbonate and 0.7 g BHT were added. 33 g (260 mmol) 3-chloro-propionylchloride was added over 15 minutes. The mixture was heated to reflux and the reaction was allowed to continue for 3 hours at reflux. The reaction mixture was allowed to cool down to room temperature and the precipitated salts were removed by filtration. The solvent was evaporated under reduced pressure and the crude 2-propenoic acid-(9-oxo-9H-thioxanthen-2-yl ester) was purified by preparative column chromatography on a Prochrom LC80 column, using Kromasil Si 60A 10μ as silica and methylene chloride as eluent. 15.6 g (43.3%) of 2-propenoic acid-(9-oxo-9H-thioxanthen-2-yl ester) was isolated.

Synthesis of Co-Initiator COINI-2

The synthesis was performed according to the following scheme:

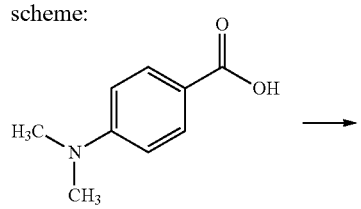

14.2 g (215 mmol) of 85% KOH was dissolved in 100 mL ethanol. The temperature rose to 30° C. 30 g (178 mmol) of 4-dimethylamino benzoic acid was added and the mixture was stirred for 90 minutes. The solvent was evaporated under reduced pressure. The residue was treated with 300 mL methyl tert. butyl ether, isolated by filtration and dried.

9.4 g (47 mmol) of 4-dimethylamino benzoic acid potassium salt was added to a solution of 10 g (56 mmol) of 2-bromoethyl acrylate in 40 mL dimethyl acetamide. 1 g of BHT was added and the mixture was heated to 60° C. for 2 hours. The reaction was allowed to cool down to room temperature. The formed potassium bromide was removed by filtration and 150 mL of methyl tert. butyl ether was added. The mixture was extracted with 150 mL of water. The organic fraction was isolated, dried over $MgSO_4$ and evaporated under reduced pressure. The residue was redissolved in 150 mL of methyl tert. butyl ether and extracted with 150 mL of a 1 M $NaHCO_3$-solution. The organic layer was dried over $MgSO_4$ and evaporated under reduced pressure. The residue was treated with water. COINI-2 precipitated from the medium, was isolated by filtration and dried. 4.3 g of COINI-2 was isolated.

Preparation of Radiation Curable Compositions

The comparative radiation curable compositions COMP-1 and COMP-2 and the inventive radiation curable compositions INV-1 to INV-7 were prepared according to Table 5. The weight % (wt %) was based on the total weight of the radiation curable compositions. Dibutyl phthalate was added to the radiation curable compositions so that it could be used as an internal reference for the analysis of extractable residues.

TABLE 5

| | w % of | | | | | | | | |
|---|---|---|---|---|---|---|---|---|---|
| | COMP-1 | COMP-2 | INV-1 | INV-2 | INV-3 | INV-4 | INV-5 | INV-6 | INV-7 |
| VEEA | 69.0 | 69.0 | 69.0 | 71.5 | 69.0 | 66.5 | 66.5 | 66.0 | 66.0 |
| M600 | 20.0 | 20.0 | 20.0 | 20.0 | 20.0 | 20.0 | 20.0 | 20.0 | 20.0 |
| IC127 | 2.5 | 2.5 | 2.5 | 2.5 | 2.5 | 2.5 | 2.5 | 2.5 | 2.5 |
| COINI-1 | 5.0 | 5.0 | 5.0 | — | — | — | — | — | — |
| COINI-2 | — | — | — | 2.5 | 5.0 | 5.0 | 5.0 | 5.0 | 5.0 |

TABLE 5-continued

| | w % of | | | | | | | | |
|---|---|---|---|---|---|---|---|---|---|
| | COMP-1 | COMP-2 | INV-1 | INV-2 | INV-3 | INV-4 | INV-5 | INV-6 | INV-7 |
| COMPINI-1 | 2.5 | — | — | — | — | — | — | — | — |
| COMPINI-2 | — | 2.5 | — | — | — | — | — | — | — |
| TX-1 | — | — | 2.5 | 2.5 | 2.5 | 5.0 | — | — | — |
| TX-2 | — | — | — | — | — | — | 5.0 | — | — |
| TX-7 | — | — | — | — | — | — | — | 5.5 | — |
| TX-5 | — | — | — | — | — | — | — | — | 5.5 |
| Dibutyl phtalate | 1.0 | 1.0 | 1.0 | 1.0 | 1.0 | 1.0 | 1.0 | 1.0 | 1.0 |

30 mg Tegorad 2100 per 100 g of both the comparative radiation curable compositions COMP-1 and COMP-2 and the inventive radiation curable compositions INV-1 to INV-7 was added.

The compatibility of both the comparative initiators COMPINI-1 and COMPINI-2 and the inventive initiators TX-1, TX-2, TX-5 and TX-7 was evaluated. The solubility results are summarized in Table 6.

TABLE 6

| Radiation curable composition | Thioxanthone solubility |
|---|---|
| COMP-1 | insoluble at room temperature, soluble at 70° C. |
| COMP-2 | insoluble, even at 70° C. |
| INV-1 | soluble at room temperature |
| INV-2 | soluble at room temperature |
| INV-3 | soluble at room temperature |
| INV-4 | soluble at room temperature |
| INV-5 | soluble at room temperature |
| INV-6 | soluble at room temperature |
| INV-7 | soluble at room temperature |

From Table 6, it should be clear that only the initiators according to preferred embodiments of the present invention have a good compatibility over a sufficient wide range of concentrations to be applicable in a broad scope of radiation curable formulations.

Evaluation of Curing Speed and Viscosity

The curing speed of the inventive radiation curable compositions INV-1 to INV-7 was evaluated. The inventive radiation curable compositions INV-1 to INV-7 were coated on a PET100 substrate using a bar coater and a 10 μm wired bar. The coatings were cured using a Fusion DRSE-120 conveyer, equipped with a Fusion VPS/1600 lamp (D-bulb), which transported the samples under the UV-lamp on a conveyer belt at a speed of 20 m/min. The curing speed was defined as the percentage of the maximum output of the lamp needed to cure the samples.

The viscosity of the formulations was measured using a Brookfield DV-II+ viscometer.

The results are summarized in Table 7 (*: measured at 45° C. at 12 rotations per minute).

TABLE 7

| Radiation curable compositions | Viscosity (mPas) | Curing speed (% of the maximum output) |
|---|---|---|
| INV-1 | 5.4* | 80 |
| INV-2 | 4.8* | 80 |
| INV-3 | 5.1* | 75 |
| INV-4 | 11.8 (5.4*) | 65 |

TABLE 7-continued

| Radiation curable compositions | Viscosity (mPas) | Curing speed (% of the maximum output) |
|---|---|---|
| INV-5 | 10.1 | 60 |
| INV-6 | 9.9 | 65 |
| INV-7 | 13.2 | 60 |

From Table 7, it becomes clear that radiation curable compositions according to preferred embodiments of the present invention all exhibit high curing speeds under ambient atmosphere and are well within the viscosity range for jettable formulations.

Evaluation of Extractable Residues

Coated samples of the radiation curable compositions INV-4 to INV-7 were prepared to determine extractable residues as described below.

The free radical curable liquids INV-4 to INV-7 were coated on a PET100 substrate using a bar coater and a 10 μm wired bar. Each coated sample was cured using a Fusion DRSE-120 conveyer, equipped with a Fusion VPS/1600 lamp (D-bulb), which transported the samples under the UV-lamp on a conveyer belt at a speed of 20 m/min. The lamp was used at its maximum output. The extraction procedure:

Two samples of 7.068 $cm^2$ of INV-4 to INV-7 were put into a 50 ml beaker and extracted with 4.5 ml acetonitrile, using ultrasound for 30 minutes at room temperature. The extract was transferred into a 5 ml volumetric flask. The samples were rinsed twice with a small amount of acetonitrile and the rinsing solvent was transferred into the 5 ml volumetric flask until the volume was adjusted to 5 ml. The solution was thoroughly mixed and filtered over a 0.45 μm filter. 15 μl of each sample was injected on the HPLC.

The Chromatographic Method:

An Alltima C18 5 μm column (150×3.2 mm), supplied by Alltech, was used. A flow rate of 0.5 ml/min was used at a temperature of 40° C. A DAD detector at 258 nm and 312 nm was used to detect the extracted initiator.

The following HPLC-method was used for all samples.

Eluent A: $H_2O$+0.02M $KH_2PO_4$ pH=2.5 using $H_3PO_4$

Eluent B: $H_2O$+0.02M $KH_2PO_4$ pH=2.5 using $H_3PO_4$/$CH_3CN$ [40/60] (v/v)

Eluent C: $H_2O$/$CH_3CN$ [40/60] (v/v)

Eluent D: $H_2O$/$CH_3CN$ [10/90] (v/v)

The gradient (end run=38 min) is shown by Table 8.

TABLE 8

| Time (min) | % eluent A | % eluent B | % eluent C | % eluent D |
|---|---|---|---|---|
| 0 | 70 | 30 | 0 | 0 |
| 6 | 70 | 30 | 0 | 0 |
| 11 | 0 | 100 | 0 | 0 |
| 20 | 0 | 100 | 0 | 0 |
| 21 | 0 | 0 | 100 | 0 |
| 24 | 0 | 0 | 100 | 0 |
| 25 | 0 | 0 | 0 | 100 |
| 30 | 0 | 0 | 0 | 100 |
| 31 | 70 | 30 | 0 | 0 |
| 38 | 70 | 30 | 0 | 0 |

The concentration was determined in comparison with a reference sample of a known concentration of each inventive initiator, eluted under the same conditions as the extracted samples. A total coating weight 10 g/m² was assumed for each sample.

The results are summarized in Table 9.

TABLE 9

| Radiation curable composition | Extractable residues (mg/m²) | % of the initiator which remains extractable |
|---|---|---|
| INV-4 | 1.2 | 0.25 |
| INV-5 | 0.7 | 0.15 |
| INV-6 | 0.4 | 0.05 |
| INV-7 | 0.4 | 0.05 |

Example 3

This example illustrates the performance of the Norrish Type II photoinitiators according to a preferred embodiment of the present invention in combination with a polymerizable co-initiator and a polymerizable Norrish Type I photoinitiator.

Preparation of Radiation Curable Compositions

The inventive radiation curable compositions INV-8 to INV-11 were prepared according to Table 10. The weight % (wt %) was based on the total weight of the radiation curable compositions. Dibutyl phthalate was added to the radiation curable compositions so that it could be used as an internal reference for the analysis of extractable residues.

TABLE 10

| wt % of | INV-8 | INV-9 | INV-10 | INV-11 |
|---|---|---|---|---|
| VEEA | 66.5 | 64.0 | 61.5 | 59.0 |
| M600 | 20.0 | 20.0 | 20.0 | 20.0 |
| Type I | 2.5 | 5.0 | 7.5 | 7.5 |
| COINI-2 | 5.0 | 5.0 | 5.0 | 7.5 |
| TX-1 | 5.0 | 5.0 | 5.0 | 5.0 |
| dibutyl phtalate | 1.0 | 1.0 | 1.0 | 1.0 |

Evaluation of Curing Speed and Viscosity

The curing speed of the inventive radiation curable compositions INV-8 to INV-11 was evaluated. The inventive radiation curable compositions INV-8 to INV-11 were coated on a PET100 substrate using a bar coater and a 10 μm wired bar. The coatings were cured using a Fusion DRSE-120 conveyer, equipped with a Fusion VPS/1600 lamp (D-bulb), which transported the samples under the UV-lamp on a conveyer belt at a speed of 20 m/min. The curing speed was defined as the percentage of the maximum output of the lamp needed to cure the samples.

The viscosity of the formulations was measured using a Brookfield DV-II+ viscometer.

The results are summarized in Table 11.

TABLE 11

| Radiation curable compositions | Viscosity (mPas) | Curing speed (% of the maximum output) |
|---|---|---|
| INV-8 | 11.1 | 90 |
| INV-9 | 11.3 | 75 |
| INV-10 | 12.2 | 60 |
| INV-11 | 16.4 | 50 |

All radiation curable compositions according to preferred embodiments of the present invention show a good to excellent curing speed under ambient atmosphere and are well within the viscosity range for jettable formulations.

Evaluation of Extractable Residues

Coated samples of radiation curable compositions INV-8 to INV-11 were prepared to determine extractable residues as described below.

The free radical curable liquids INV-8 to INV-11 were coated on a PET100 substrate using a bar coater and a 10 μm wired bar. Each coated sample was cured using a Fusion DRSE-120 conveyer, equipped with a Fusion VPS/1600 lamp (D-bulb), which transported the samples under the UV-lamp on a conveyer belt at a speed of 20 m/min. The lamp was used at its maximum output.

The Extraction Procedure:

Two samples of 7.068 cm² of INV-8 to INV-11 were put into a 50 ml beaker and extracted with 4.5 ml acetonitrile, using ultrasound for 30 minutes at room temperature. The extract was transferred into a 5 ml volumetric flask. The samples were rinsed twice with a small amount of acetonitrile and the rinsing solvent was transferred into the 5 ml volumetric flask until the volume was adjusted to 5 ml. The solution was thoroughly mixed and filtered over a 0.45 μm filter. 15 μl of each sample was injected on the HPLC.

The Chromatographic Method:

An Alltima C18 5 μm column (150×3.2 mm), supplied by Alltech, was used. A flow rate of 0.5 ml/min was used at a temperature of 40° C. A DAD detector at 291 nm was used to detect the extracted initiators and the coinitiator.

The following HPLC-method was used for all samples.
Eluent A: $H_2O+0.02M$ $KH_2PO_4$ pH=2.5 using $H_3PO_4$
Eluent B: $H_2O+0.02M$ $KH_2PO_4$ pH=2.5 using $H_3PO_4$/$CH_3CN$ [40/60] (v/v)
Eluent C: $H_2O/CH_3CN$ [40/60] (v/v)
Eluent D: $H_2O/CH_3CN$ [10/90] (v/v)
The gradient (end run=38 min) is shown by Table 12.

TABLE 12

| Time (min) | % eluent A | % eluent B | % eluent C | % eluent D |
|---|---|---|---|---|
| 0 | 70 | 30 | 0 | 0 |
| 6 | 70 | 30 | 0 | 0 |
| 11 | 0 | 100 | 0 | 0 |
| 20 | 0 | 100 | 0 | 0 |
| 21 | 0 | 0 | 100 | 0 |
| 24 | 0 | 0 | 100 | 0 |
| 25 | 0 | 0 | 0 | 100 |
| 30 | 0 | 0 | 0 | 100 |
| 31 | 70 | 30 | 0 | 0 |
| 38 | 70 | 30 | 0 | 0 |

The concentration was determined in comparison with a reference sample of a known concentration of each initiator and co-initiator, eluted under the same conditions as the extracted samples. A total coating weight 10 g/m² was assumed for each sample. The results are summarized in Table 13.

TABLE 13

| Radiation curable composition | Extractable amount of: (expressed as % which remains extractable) | | |
|---|---|---|---|
| | TX-1 | Type I | COINI-2 |
| INV-8 | 1.3 | 1.2 | 0.4 |
| INV-9 | 0.9 | 0.9 | 0.3 |
| INV-10 | 0.8 | 0.9 | 0.3 |
| INV-11 | 0.9 | 1.5 | 0.6 |

From Table 13, it becomes clear that only minor fractions of both the initiators and the co-initiator remain extractable.

While preferred embodiments of the present invention have been described above, it is to be understood that variations and modifications will be apparent to those skilled in the art without departing the scope and spirit of the present invention. The scope of the present invention, therefore, is to be determined solely by the following claims.

The invention claimed is:

1. A polymerizable Norrish Type II photoinitiator according to Formula (I):

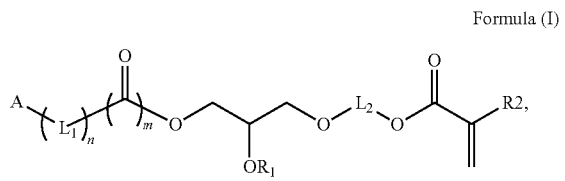

Formula (I)

wherein
A represents a Norrish Type II initiator selected from the group consisting of an unsubstituted benzophenone and an optionally substituted thioxanthone;
$L_1$ represents a divalent linking group selected from the group consisting of —O—CH₂— and —O—CH(CH₃);
n represents 0 or 1;
m represents 0 or 1, with the proviso that n is equal to 0, when m is equal to 0;
R1 is selected from the group consisting of a hydrogen, an optionally substituted alkyl group, an optionally substituted alkenyl group, an optionally substituted alkynyl group, an optionally substituted alkaryl group, an optionally substituted aralkyl group, an optionally substituted aryl group, an optionally substituted heteroaryl group, and an acyl group;
R2 represents hydrogen or a methyl group;
$L_2$ represents a divalent linking group selected from the group consisting of an unsubstituted saturated alkylene group, an unsubstituted unsaturated alkylene group, an unsubstituted arylene group, and a group represented by Formula (II):

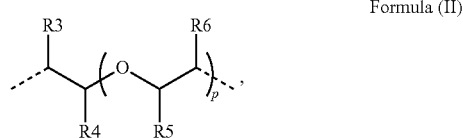

Formula (II)

and
R3 to R6 independently represent hydrogen or a methyl group; and
p represents an integer from 1 to 10.

2. The polymerizable Norrish Type II photoinitiator according to claim 1, wherein the integer n is 0.

3. The polymerizable Norrish Type II photoinitiator according to claim 1, wherein $L_2$ represents an substituted saturated alkylene group.

4. The polymerizable Norrish Type II photoinitiator according to claim 2, wherein $L_2$ represents an unsubstituted saturated alkylene group.

5. The polymerizable Norrish Type II photoinitiator according to claim 3, wherein R2 represents hydrogen.

6. The polymerizable Norrish Type II photoinitiator according to claim 4, wherein R2 represents hydrogen.

7. A polymerizable Norrish Type II photoinitiator selected from the group consisting of:

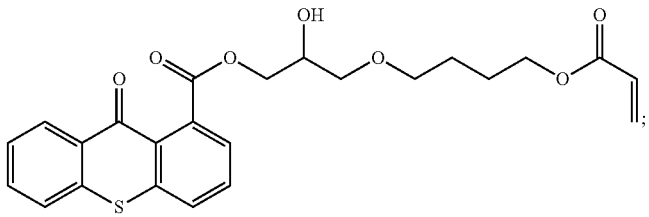

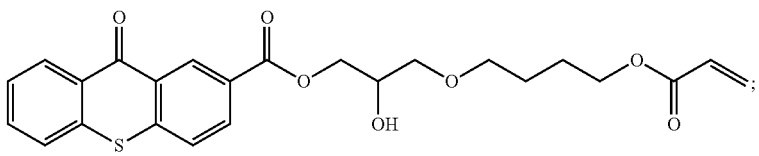

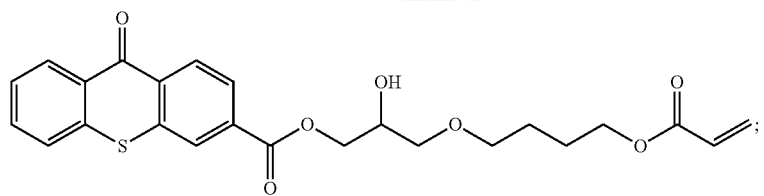
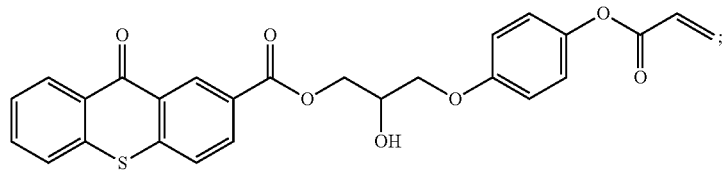
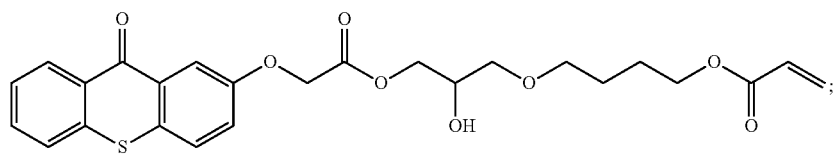
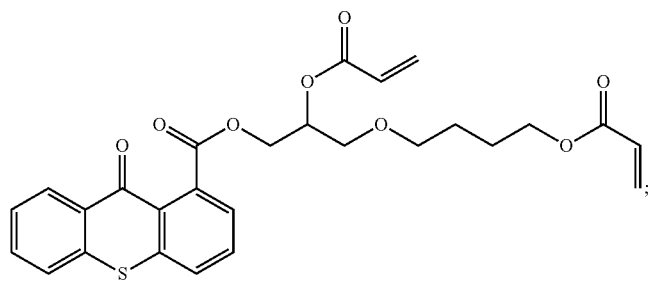
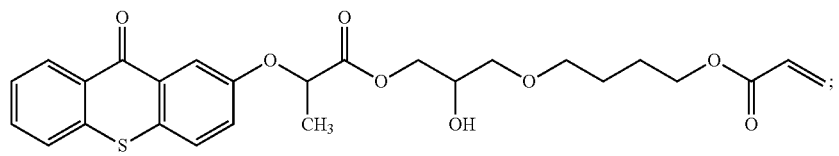
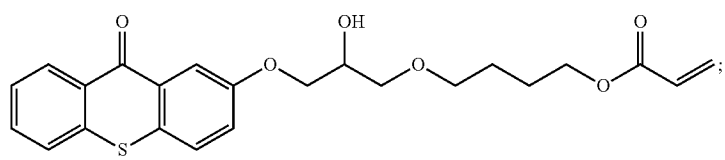
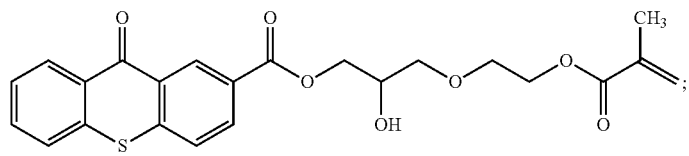
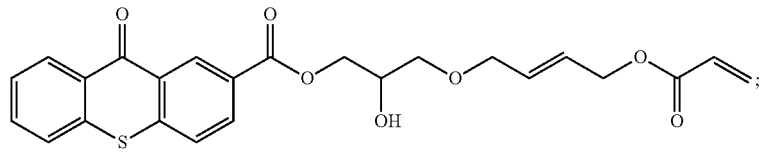
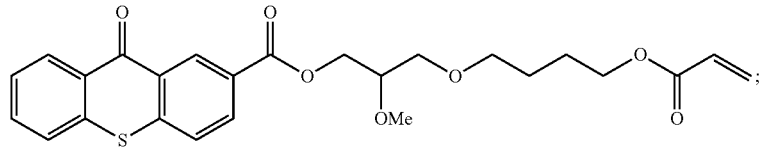

-continued

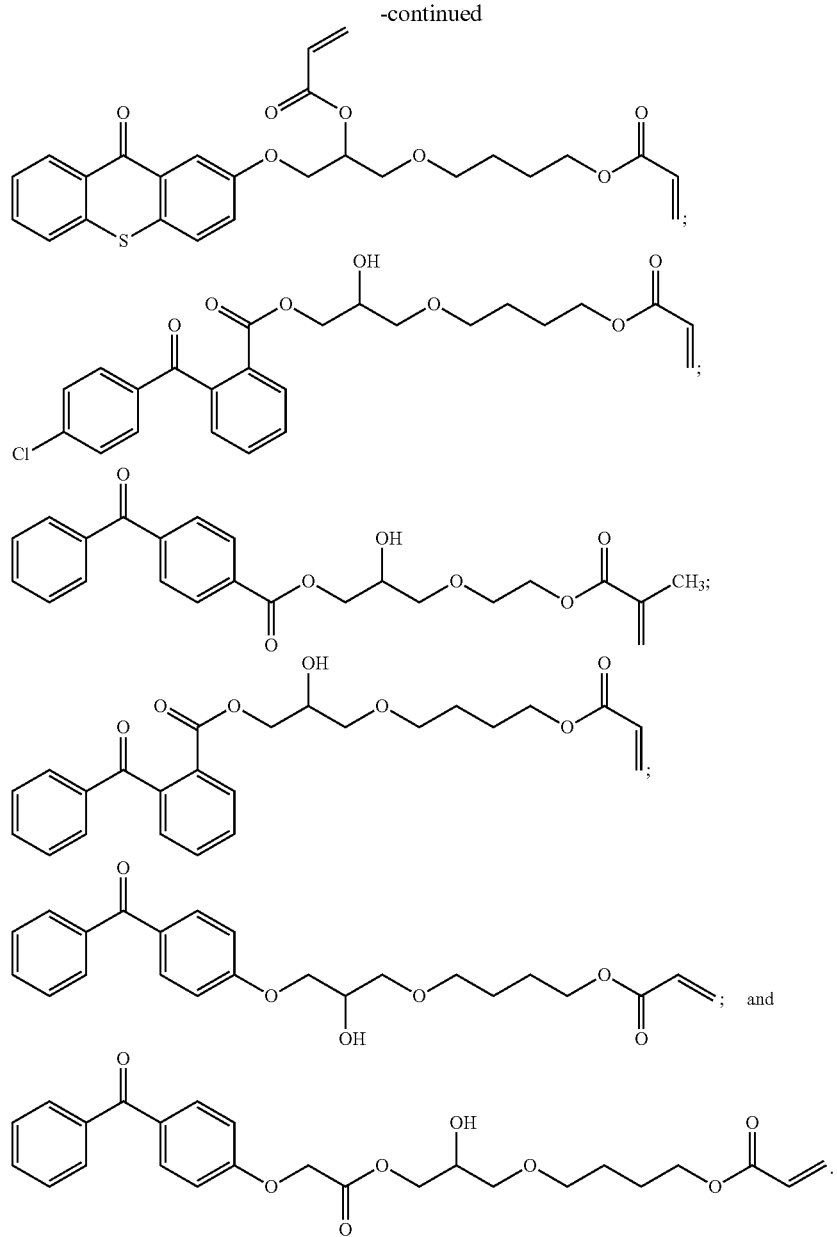

8. A radiation curable composition comprising:
a polymerizable Norrish Type II-photoinitiator as defined by claim 1; and
at least one co-initiator; wherein
the co-initiator is selected from the group consisting of a polymeric dialkylamino substituted aromatic compound, a multifunctional dialkylamino substituted aromatic compound, and a dialkylamino substituted aromatic compound comprising at least one ethylenically unsaturated polymerizable group.

9. The radiation curable composition according to claim 8, wherein the co-initiator comprises one ethylenically unsaturated polymerizable group.

10. The radiation curable composition according to claim 8, further comprising a colorant.

11. A radiation curable inkjet ink comprising:
the radiation curable composition according to claim 8.

12. A radiation curable inkjet ink comprising:
the radiation curable composition according to claim 9.

13. A radiation curable inkjet ink comprising:
the radiation curable composition according to claim 10.

14. An inkjet printing method comprising the steps of:
applying a radiation curable composition according to claim 8 to a substrate by flexographic printing;
at least partially curing the radiation curable composition; and
printing an inkjet ink upon the at least partially cured radiation curable composition previously applied on the substrate.

15. An inkjet printing method comprising the steps of:
jetting a radiation curable composition according to claim 8 upon a substrate; and
at least partially curing the radiation curable composition previously jetted upon the substrate.

* * * * *

UNITED STATES PATENT AND TRADEMARK OFFICE
CERTIFICATE OF CORRECTION

PATENT NO.        : 8,530,510 B2
APPLICATION NO.   : 13/060278
DATED             : September 10, 2013
INVENTOR(S)       : Johan Loccufier et al.

It is certified that error appears in the above-identified patent and that said Letters Patent is hereby corrected as shown below:

In the Claims

Please correct the wording on line 34, Claim 3, column 48 of the patent as follows:

'...an substituted...' should read '...an unsubstitued...'

Signed and Sealed this
Fourth Day of February, 2014

Michelle K. Lee
*Deputy Director of the United States Patent and Trademark Office*